(12) United States Patent
Perkins et al.

(10) Patent No.: US 8,033,462 B2
(45) Date of Patent: Oct. 11, 2011

(54) WIRELESS TRACKING SYSTEM AND METHOD FOR STERILIZABLE OBJECT

(75) Inventors: Matthew R. Perkins, San Diego, CA (US); Eric Hoffman, Santee, CA (US); Robert Shein, El Cajon, CA (US)

(73) Assignee: Awarepoint Corporation, San Diego, CA (US)

( * ) Notice: Subject to any disclaimer, the term of this patent is extended or adjusted under 35 U.S.C. 154(b) by 0 days.

(21) Appl. No.: 12/484,234

(22) Filed: Jun. 14, 2009

(65) Prior Publication Data

US 2010/0252627 A1     Oct. 7, 2010

Related U.S. Application Data

(60) Provisional application No. 61/165,869, filed on Apr. 1, 2009.

(51) Int. Cl.
   *G06F 19/00*     (2011.01)
(52) U.S. Cl. ......... 235/385; 235/375; 235/487; 235/492
(58) Field of Classification Search .................. 235/375, 235/385, 487, 492; 340/10, 572
   See application file for complete search history.

(56) References Cited

U.S. PATENT DOCUMENTS

| | | | |
|---|---|---|---|
| 5,424,048 A | 6/1995 | Riley | |
| 6,037,879 A | 3/2000 | Tuttle | |
| 6,255,949 B1* | 7/2001 | Nicholson et al. | 340/572.8 |
| 6,294,997 B1 | 9/2001 | Paratore et al. | |
| 6,634,499 B2 | 10/2003 | Allen et al. | |
| 6,712,276 B1 | 3/2004 | Abali et al. | |
| 6,827,913 B2 | 12/2004 | Wood | |
| 6,991,761 B2* | 1/2006 | Hehenberger et al. | 422/3 |
| 7,118,029 B2 | 10/2006 | Nycz et al. | |
| 7,573,382 B2* | 8/2009 | Choubey et al. | 340/539.13 |
| 2002/0032435 A1* | 3/2002 | Levin | 606/1 |
| 2006/0208881 A1* | 9/2006 | Suzuki | 340/539.27 |
| 2006/0244597 A1* | 11/2006 | Tethrake et al. | 340/572.1 |
| 2007/0094303 A1* | 4/2007 | Zwingenberger et al. | 707/104.1 |
| 2007/0272746 A1 | 11/2007 | Ortiz et al. | |
| 2008/0024310 A1* | 1/2008 | Baker et al. | 340/572.8 |
| 2008/0030345 A1* | 2/2008 | Austin et al. | 340/572.8 |
| 2008/0145919 A1 | 6/2008 | Franklin et al. | |
| 2008/0296373 A1* | 12/2008 | Zmood et al. | 235/385 |
| 2009/0009288 A1* | 1/2009 | Fogg | 340/10.1 |
| 2009/0134997 A1* | 5/2009 | Godlewski | 340/539.1 |
| 2009/0289792 A1* | 11/2009 | Potyrailo et al. | 340/572.1 |

FOREIGN PATENT DOCUMENTS

| | | |
|---|---|---|
| JP | 2007-026302 A | 2/2007 |
| JP | 2007-133617 A | 5/2007 |

OTHER PUBLICATIONS

International Search Report and Written Opinion for PCT/US2010/028976 a related PCT application.

* cited by examiner

*Primary Examiner* — Michael G Lee
*Assistant Examiner* — Matthew Mikels
(74) *Attorney, Agent, or Firm* — Clause Eight IPS; Michael Catania

(57) ABSTRACT

The present invention is a method for real-time location monitoring of a sterilizable object. The method includes tracking a location of a sterilizable object bearing a tag. The tag includes a sealed housing, means for detecting a sterilization event and means for transmitting data concerning the sterilization event. The method also includes detecting a sterilization event. The method also includes transmitting a signal that the sterilization event has been detected by the tag.

5 Claims, 20 Drawing Sheets

WIRELESS TRACKING SYSTEM AND METHOD FOR STERILIZABLE OBJECT

CROSS REFERENCES TO RELATED APPLICATIONS

The present application claims priority to U.S. Provisional Patent Application No. 61/165,869, filed on Apr. 1, 2009.

STATEMENT REGARDING FEDERALLY SPONSORED RESEARCH OR DEVELOPMENT

Not Applicable

BACKGROUND OF THE INVENTION

1. Field of the Invention

The present invention is related to wireless tracking systems and methods. More specifically, the present invention relates to a wireless tracking system and method for a tag subject to extreme temperatures.

2. Description of the Related Art

The ability to quickly determine the location of objects located within a facility is becoming a necessity of life. To the uninformed observer, the placement of transponders, also known as tags, on numerous non-stationary objects whether in an office or home would appear to be an unnecessary use of resources. However, the uninformed observer fails to appreciate the complexity of modern life and the desire for efficiency, whether at the office or home.

For example, in a typical hospital there are numerous shifts of employees utilizing the same equipment. When a new shift arrives the ability to quickly locate medical equipment not only results in a more efficient use of resources, but also can result in averting a medical emergency. Thus, the tracking of medical equipment in a hospital is becoming a standard practice.

The tracking of objects in other facilities is rapidly becoming a means of achieving greater efficiency. A typical radio frequency identification system includes at least multiple tagged objects, each of which transmits a signal, multiple receivers for receiving the transmissions from the tagged objects, and a processing means for analyzing the transmissions to determine the locations of the tagged objects within a predetermined environment.

Medical equipment subject to extreme temperatures includes surgical kits or surgical trays which are typically sterilized in an autoclave at high temperatures to destroy any living organisms (bacteria, fungi, viruses and spores). Autoclaves generally use heat and high pressure to destroy the living organisms. These high temperatures are often in excess of 120 degrees Fahrenheit, and as high as 300 degrees Fahrenheit.

The surgical trays are typically composed of stainless steel, aluminum or another metal. Various surgical instruments are contained within the surgical tray. An example of such a tray is disclosed in Wood, U.S. Pat. No. 6,827,913, for a Modular Sterilization Tray Systems For Medical Instruments.

The autoclave sterilization temperatures are far beyond the typically room temperature operating ranges for most RFID tags or similar wireless tracking tags. However, there is a need to track the location of the surgical trays since the ability to monitor the location and the sterilization status of such surgical trays allows a hospital or other like facility to adequately prepare for a surgery procedure.

Nycz, et al., U.S. Pat. No. 7,118,029, for a Smart Instrument Tray RFID Reader, discloses the use of passive RFID tags that are attached to surgical instruments to provide information on the contents of a surgical tray. The RFID tags can be encased in such materials as Phenol, Glass, Wood, Epoxy resin, Silicon, Rubber, Polyvinyl Chloride, Acrylonitrile Butadiene Styrene, common plastic and Styrofoam.

Nicholson, et al., U.S. Pat. No. 6,255,949, for a High Temperature RFID Tag, discloses an RFID tag that is capable of withstanding temperatures of −40 degrees Celsius to 300 degrees Celsius. The tag is placed within a housing composed of a high thermally resistant material such as RYTON PPS compound or TEFLON.

Although the prior art has provided numerous solutions, the prior art has failed to recognize the problems associated with wireless location asset tracking in a sterilization environment.

BRIEF SUMMARY OF THE INVENTION

The present invention has recognized that operating a wireless tracking system in a sterilization environment creates unique problems. The present invention provides a solution by transmitting a sterilization event alert.

One aspect of the present invention is a method for real-time location monitoring of a sterilizable object. The method includes tracking a location of a sterilizable object bearing a tag. The tag includes a sealed housing, means for detecting a sterilization event and means for transmitting data concerning the sterilization event. The method also includes detecting a sterilization event. The method also includes transmitting a signal that the sterilization event has been detected by the tag.

Optionally, the method further includes measuring the sterilization event. Optionally, the method further includes measuring the sterilization event comprises measuring the time and temperature during the sterilization event. Optionally, the method further includes associating the sterilizable object with a mobile object. Alternatively, the method includes associating the sterilizable object with a fixed object such as an autoclave, a surgery room or a surgery department. Optionally, the method further includes initiating a new process with the sterilization event is detected. Optionally, the method further includes updating a user interface.

The sterilization event is preferably a pressure change in the housing, a detection of ultrasonic energy, a detection of moisture within the housing, a predetermined pH level of a chemical in a sterile bath, detecting a gas, an electrical change in an electrical profile of the tag, the housing being compromised, duration at a predetermined temperature, duration in a single location having a predetermined temperature, a specific set of events comprising location in a sterilization zone, stationary in the sterilization zone for a predetermined time or detection of a predetermined temperature for a predetermined time period, and an order of events such as a work flow.

Another aspect of the present invention is a system for real-time location monitoring of a sterilizable object. The system includes a tracking tag, network sensors and a processing means. The tracking tag is attached to a sterilizable object. The tracking tag includes a sealed housing, means for detecting a sterilization event, means for transmitting data concerning the sterilization event outside of the housing. The network sensors are positioned within an indoor facility with at least one of the sensors receiving data from the tracking tag. The processing means processes signals from the tracking tag.

Preferably, the processing means is a remote server in communication with the network sensors, and the remote server further includes means for initiating a new process when a sterilization event is detected, means for associating the sterilizable object with a mobile object, means for adding data to a database, means for updating a user interface, and means for changing the state of a process. The sterilizable object is preferably a surgical kit. Alternatively, the sterilizable object is a surgical tool, a patient worn device, or a device exposed to non-sterile elements.

Another aspect of the present invention is a tag for real-time location monitoring of a sterilizable object. The tag includes a housing, a processor and a power supply. The processor includes a transceiver for transmitting a signal through the housing and means for detecting a sterilization event. The power supply is in electrical communication with the processor and preferably within the housing. The housing is preferably a moisture-proof housing, a gas-proof housing a pressure-proof housing, or a combination of all. The power supply preferably extracts environmental energy in the form of solar energy or motion energy. The sterilization detection means is preferably an integrated circuit of the processor. The sterilization detection means is alternatively a separate component in electrical communication with the processor.

Another aspect of the present invention is a method for real-time location monitoring of a sterilizable object in a sterilization area. The sterilization area is preferably a specific area of a hospital but alternatively is an entire hospital or multiple hospitals since items such as surgical equipment is transferred between hospitals. The method includes receiving at at least one of a plurality of sensors a tracking signal from a tag that a sterilizable object is located in a sterilization area. The tag is associated with the sterilizable object. The method also includes receiving at at least one of the plurality of sensors a first status signal from the tag that a sterilization threshold value for a sterilization event is present. The method also includes transmitting the first status signal from the at least one of the plurality of sensors to a remote server. The method also includes receiving at at least one of the plurality of sensors a second status signal from the tag that the sterilization threshold value for a sterilization event is absent. The method also includes transmitting the second status signal from the at least one of the plurality of sensors to a remote server. The method also includes determining a sterilization status for the sterilizable object at the remote server based on at least the first status signal and the second status signal. The method also includes communicating the sterilization status for the sterilizable object to an operator. The sterilization status is preferably a message that the sterilization was complete or incomplete. Alternatively the sterilization status is a message including details of the sterilization event such as the duration at each temperature, the time the sterilizable object entered the sterilization area, the person in control of the sterilizable object upon entering the sterilization area, and when the timeframe for each stage of the process for the sterilizable object.

The sterilization event is preferably one of ultrasonic energy sterilization, steam sterilization, heat sterilization, pressure sterilization, chemical sterilization and hot water sterilization. An ultrasonic energy sterilization has a sterilization threshold value of a detection of a pre-established amount of ultrasonic energy. A steam sterilization preferably has a sterilization threshold value of a detection of water vapor at a temperature of at least 100° C. A heat sterilization preferably has a sterilization threshold value of a detection of a temperature of at least 140° C. A pressure sterilization preferably has a sterilization threshold value of a detection of a pressure of at least 1.036 Bar above atmospheric pressure. A chemical sterilization preferably has a sterilization threshold value of a detection of a pH of no more than 3. Another chemical sterilization preferably has a sterilization threshold value of a detection of hydrogen peroxide in a concentration amount of at least 6%. A hot water sterilization preferably has a sterilization threshold value of a detection of liquid water at a temperature of at least 70° C. Optionally, a warning threshold represents a second threshold that is higher or lower than the sterilization event threshold. Those skilled in the pertinent art will recognize that the afore-mentioned thresholds may be adjusted to meet the needs of the sterilizable object without departing from the scope and spirit of the present invention.

The housing is preferably composed of a polyetherimide resin material.

The tracking tag preferably transmits a radiofrequency transmission of approximately 2.48 GigaHertz, and each of the plurality of network sensors communicates utilizing a 802.15.4 protocol. Alternatively, the tracking tag transmits an ultrasound or infrared transmission.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
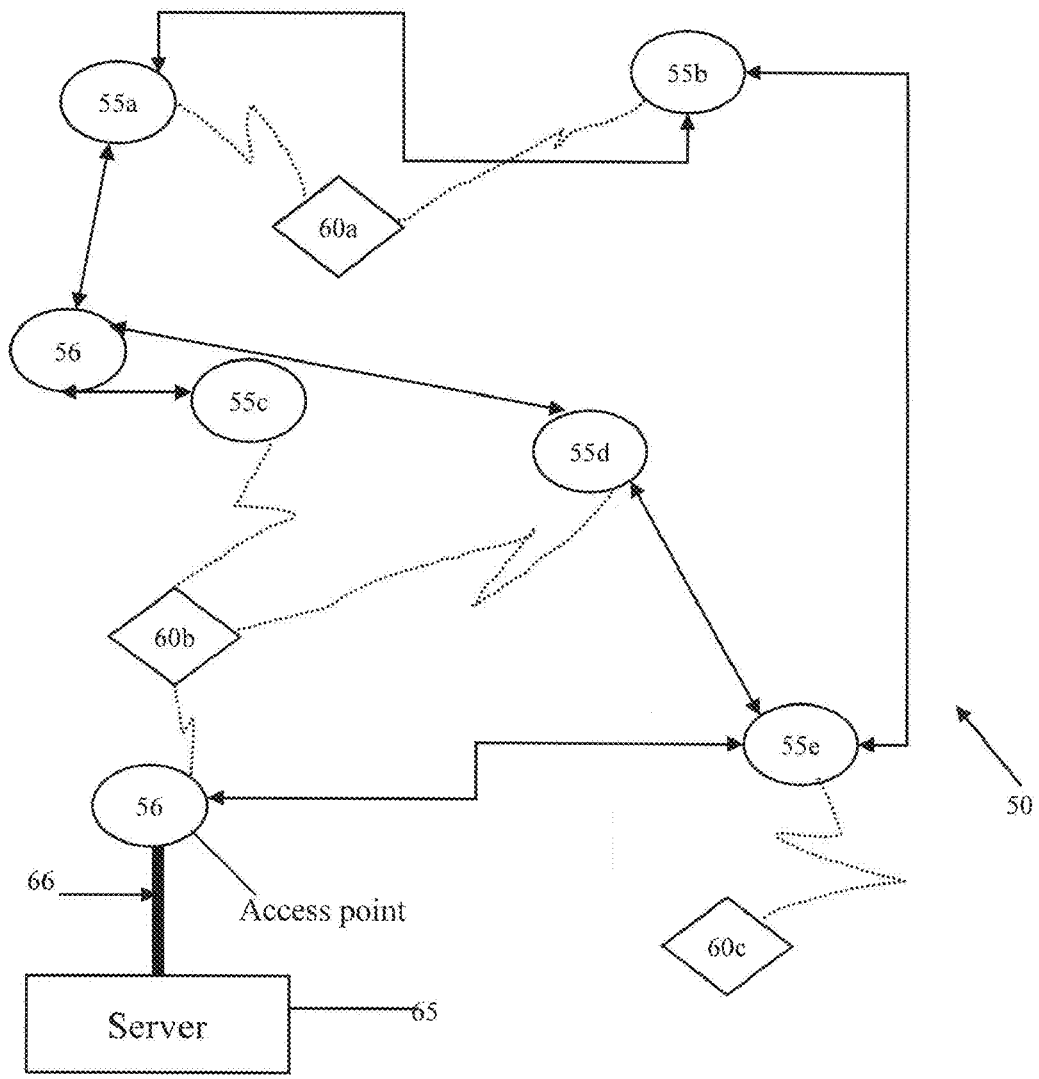
FIG. 1 is schematic view of a wireless asset tracking system.
Figure 2:
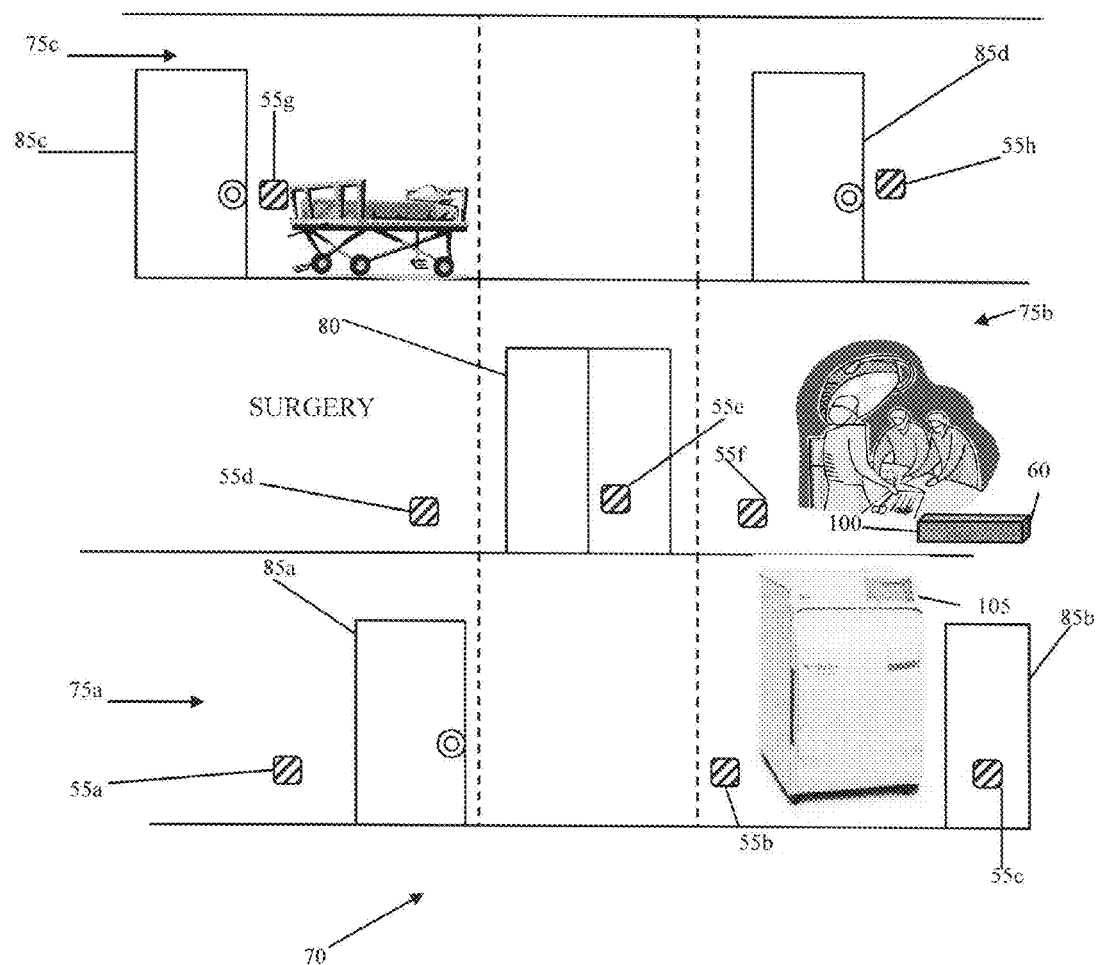
FIG. 2 is a multi-floor view of a facility employing a wireless asset tracking system.

As shown in FIGS. 1-2, a wireless asset tracking system is generally designated 50. The system 50 is capable of determining real-time location of a sterilizable object 100 within a facility 70, and is particularly useful for tracking a sterilizable object 100 that sterilized in a sterilization area of the facility 70. The system 50 preferably includes a plurality of sensors 55, a plurality of bridges 56, a plurality of tags 60 and at least one server 65. One example of the components of the system 50 is disclosed in Smith et al., U.S. Pat. No. 7,312,752 for a Wireless Position Location And Tracking System, which is hereby incorporated by reference in its entirety. A more specific example of the sensors 55 is disclosed in Smith et al., U.S. Pat. No. 7,324,824 for a Plug-In Network Appliance, which is hereby incorporated by reference in its entirety.

The system 50 is preferably employed within a facility 70 such as a hospital or other like facility. The system 50 is utilized to track and locate various sterilizable objects 100 positioned throughout the facility 70. The tags 60 preferably continuously transmit signals on a predetermined time cycle, and these signals are received by the sensors 55 positioned throughout the facility 70. Alternatively, the tags 60 transmit signals in a random, ad-hoc or dynamic manner, and these signals are received by the sensors 55 positioned throughout the facility 70. In a preferred embodiment, the tags 60 transmit a signal every five seconds when in motion, and a signal every ten minutes when stationary. The sensors 55 preferably transmit the data to a bridge 56 for transmission to a server 65. If a sensor 55 is unable to transmit to a bridge 56, the sensor 55 may transmit to another sensor 55 in a mesh network-like system for eventual transmission to a bridge 56. In a preferred embodiment, a transmission can be relayed from a sensor 55 to a bridge 56 up to a transmission distance of six sensors 55 from the bridge 56. The server 65 preferably continuously receives transmissions from the sensors 55 via the bridges 56 concerning the movement of assets 100 bearing a tag 60 within the facility 70. The server 65 processes the transmissions from the sensors 55 and calculates a real-time position for each of the assets 100 bearing a tag 60 within the facility 70. The real-time location information for each of the assets 100 bearing a tag 60 is preferably displayed on an image of a floor plan of the indoor facility 70, or if the facility 70 has multiple floors, then on the floor plan images of the floors of the facility 70. The floor plan image may be used with a graphical user interface so that an individual of the facility 70 is able to quickly locate assets 100 within the facility 70.

Figure 3:
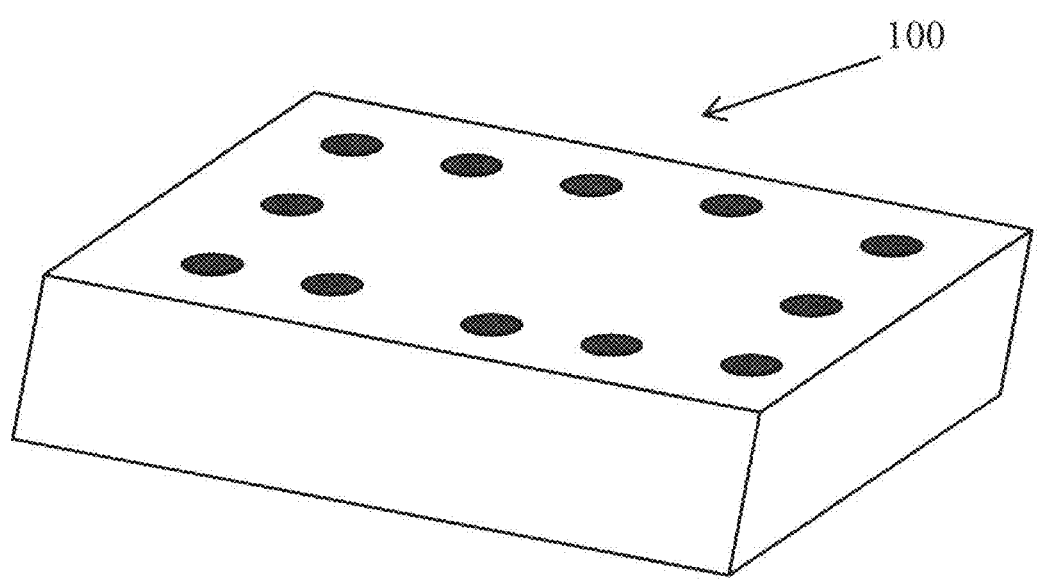
FIG. 3 is an illustration of a surgical tray.
Figure 3A:
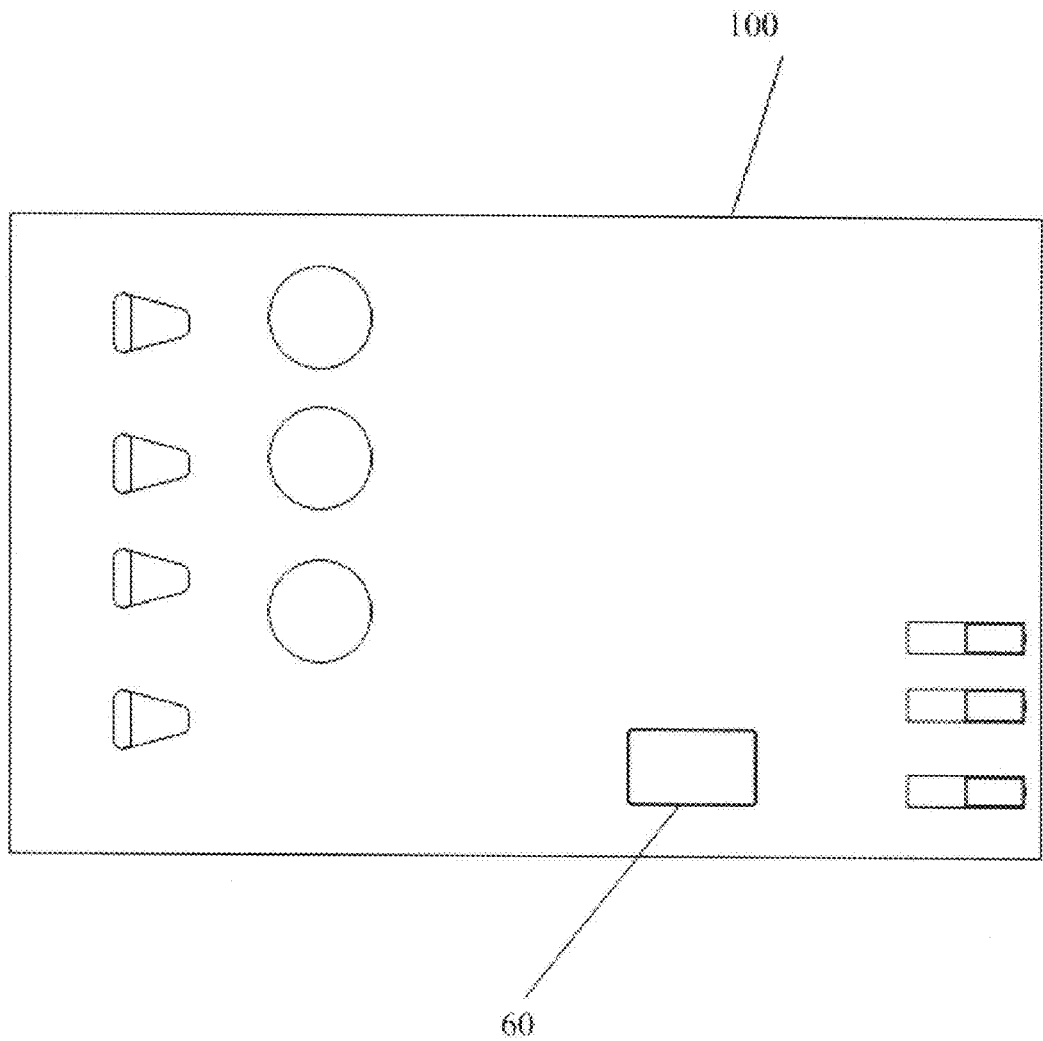
FIG. 3A is an illustration of an interior of a surgical tray.

The sterilizable objects 100 are preferably items of value to the owners or users of the system 50 and/or the facility 70. In a hospital setting, the sterilizable objects 100 could include surgical equipment, nursing equipment and the like. In particular for the present invention, the sterilizable objects 100 include surgical trays which preferably contain surgical instruments, such as shown in FIGS. 3 and 3A. Sterilization is generally defined as a process which achieves the complete killing of all microorganisms, especially bacterial spores. As used herein, sterilization is defined in a broader sense to include cleaning, disinfecting and sterilizing.

As shown in FIG. 1, the system 50 utilizes sensors 55 to monitor and identify the real-time position sterilizable objects 100 bearing or integrated with tags 60. The sensors 55a-f preferably wirelessly communicate with each other (shown as double arrow lines) and with a server 65 through a wired connection 66 via at least one bridge 56, such as disclosed in the above-mentioned U.S. Pat. No. 7,324,824 for a Plug-In Network Appliance. The tags 60a-c transmit signals (shown as dashed lines) which are received by the sensors 55a-e, which then transmit signals to bridges 56 for eventual transmission to a server 65. The server 65 is preferably located on-site at the facility 70. However, the system 50 may also include an off-site server 65, not shown.

Each tag 60 preferably transmits a radio frequency signal of approximately 2.48 GigaHertz ("GHz"). The communication format is preferably IEEE Standard 802.15.4. Those skilled in the pertinent art will recognize that the tags 60 may operate at various frequencies without departing from the scope and spirit of the present invention.

As shown in FIG. 2, the facility 70 depicted is a hospital. The facility 70 has a multitude of floors 75a-c. An elevator 80 provides access between the various floors 75a, 75b and 75c. Each floor 75a, 75b and 75c has a multitude of rooms 90a-i, with each room 90 accessible through a door 85. Positioned throughout the facility 70 are sensors 55a-o for obtaining readings from tags 60a-d attached to or integrated into non-stationary assets 100. A bridge 56 is also shown for receiving transmissions from the sensors 55 for processing by the server 65. Specifically, a surgical tray 100 is used in surgery. A tag 60 is placed inside the tray 100 in order to track the tray within the facility. The tray 100 is sent to an autoclave 105 on a lower floor of the facility for sterilization subsequent to the surgery procedure. The movement of the tray 100 is tracked by the tag 60 and the tracking system 50 of the present invention.

Figure 4:
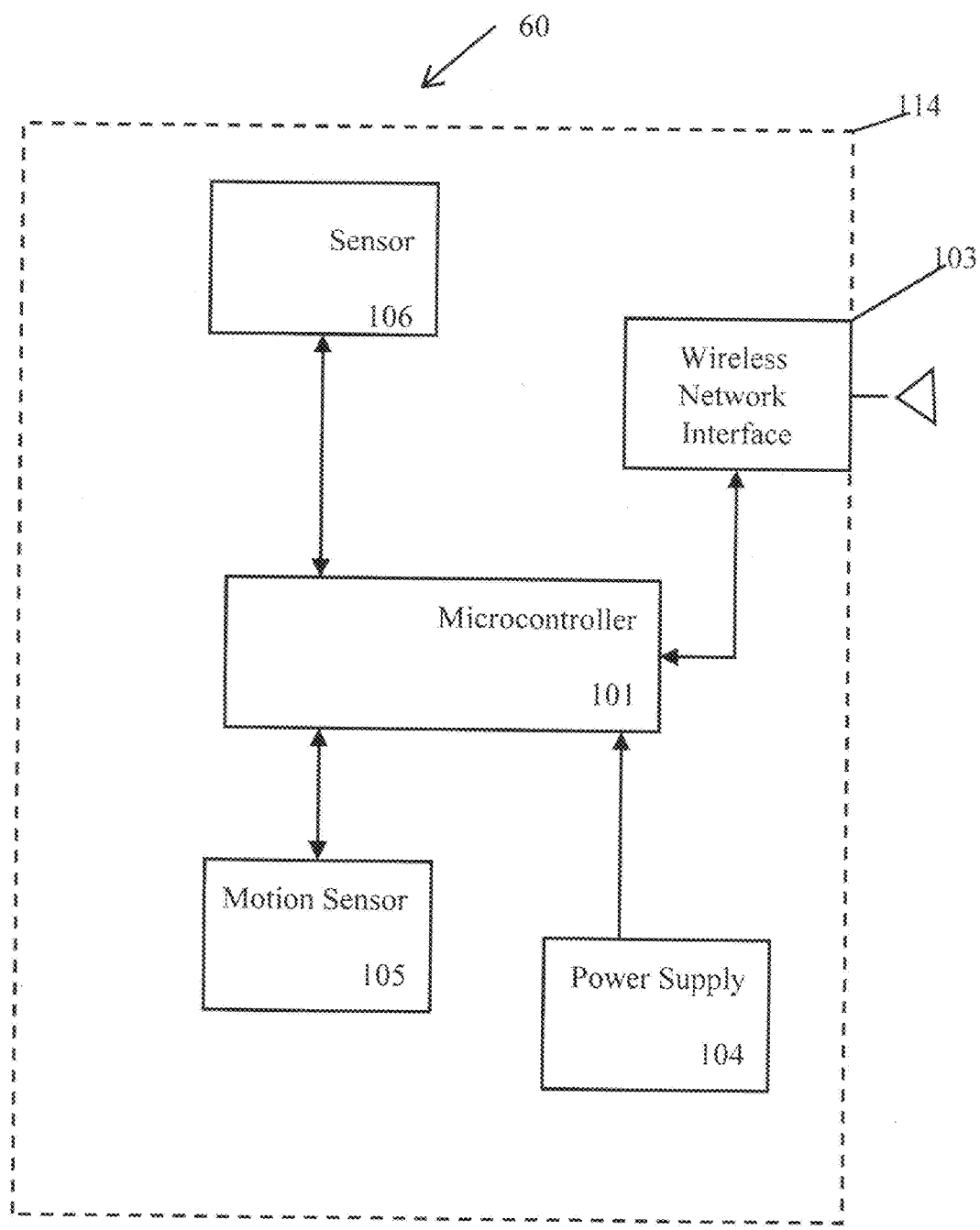
FIG. 4 is a block diagram of a tag.

As shown in FIG. 4, a tag 60 preferably includes a microcontroller or processor 101, a wireless network interface 103 having an antenna, a power supply 104, a motion sensor 105 and a sensor 106. The processor 101 is in communication with the sensor 106, motion sensor 105 and wireless network interface 103. The power supply 104 preferably provides power to the processor 101, the motion sensor 104, the sensor 106 and the wireless network interface 103. The power supply 104 is preferably a battery such as a lithium battery. The power supply 104 is preferably the only source of power for the tag 60. Conserving the energy use of the tag 60 allows the tag 60 to have greater use period before needing to be recharged or replaced.

Figure 4A:
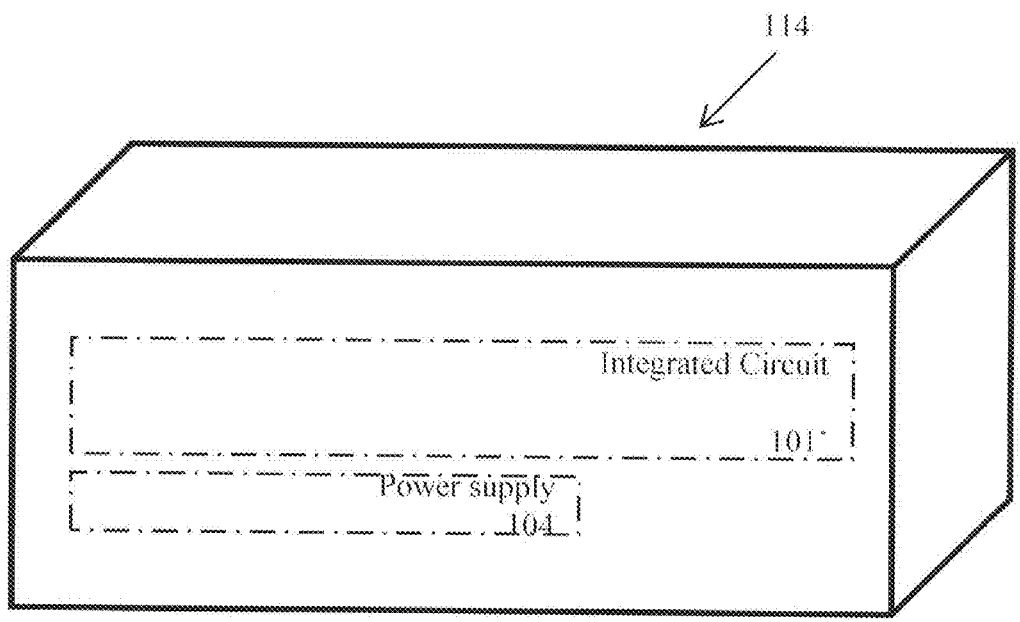
FIG. 4A is a tag with an integrated circuit.
Figure 4B:
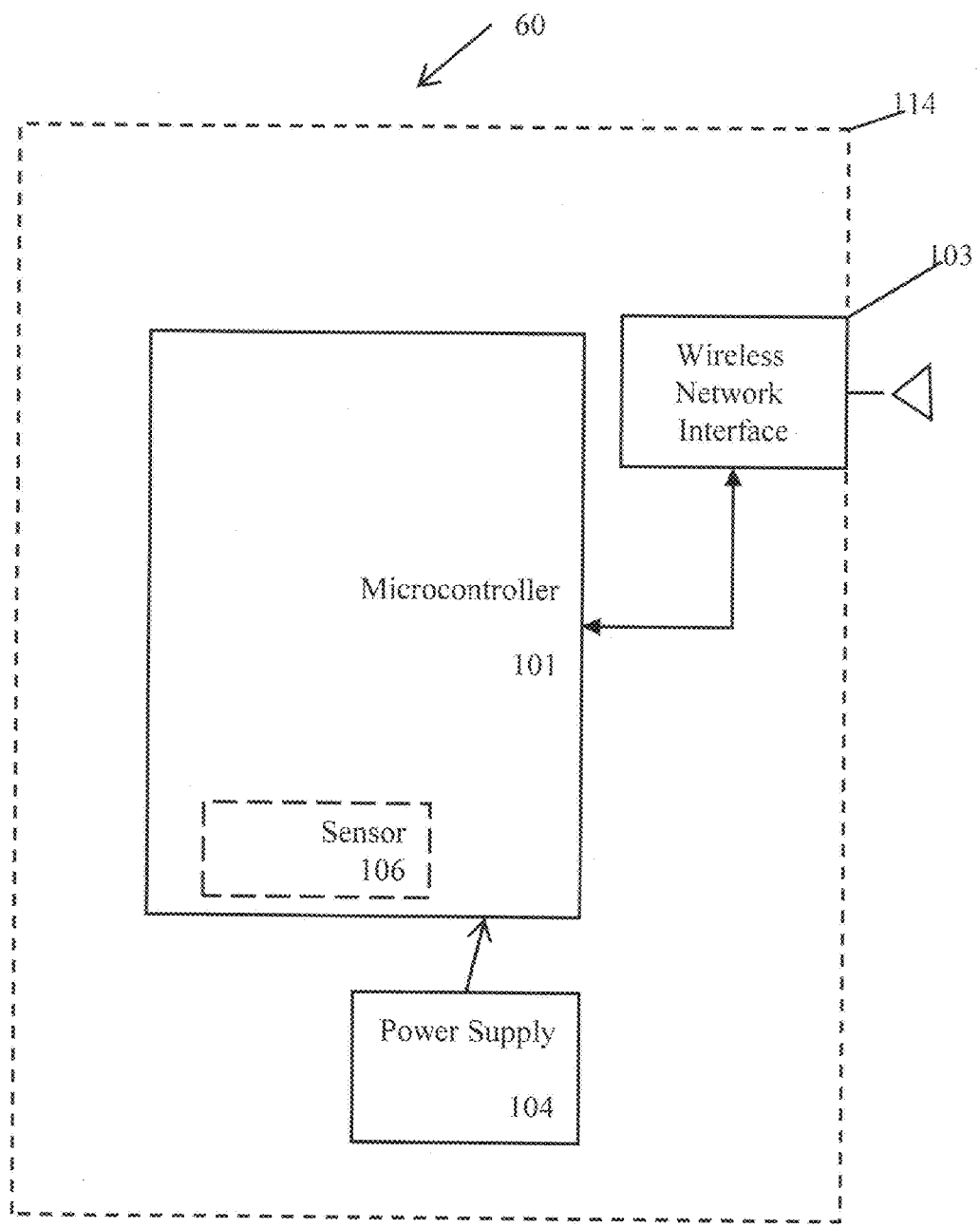
FIG. 4B is a block diagram of an alternative embodiment of a tag with an integrated circuit.

In an alternative embodiment shown in FIG. 4B, the sensor 106 is an integral component of the microcontroller 101.

Preferably the components of the tag are enclosed within a housing 114 indicated by the dashed line. The housing 114 is preferably composed of an extreme temperature resistant and moisture resistant material. A most preferred material is ULTEM polyetherimide resin, available from GE Plastics. The electrical components of the tag 60 are preferably contained within the housing 114, and the housing 114 is preferably ultrasonically welded. The housing 114 preferably has dimensions of 1 inch width by 1.6 inches length by 0.5 inch thickness. The housing 114 is preferably pneumatically leak tested to verify the ultrasonic weld. Those skilled in the pertinent art will recognize that the dimensions of the housing 114 may be adapted to a tag for various sterilizable objects without departing from the scope and spirit of the present invention.

As shown in FIG. 4A, the tag 60 has a housing 114 with an integrated circuit 101' and power supply 104 therein. The integrated circuit 101' preferably includes a microcontroller or processor, a wireless network interface having an antenna, a motion sensor, a temperature sensor, and an analog-to-digital converter. In a most preferred embodiment, the electrical components of the tag 60 are on a single integrated circuit, which are available from various commercial sources such as Texas Instruments. The power consumption is lower in a sleep mode than in an active mode. Those skilled in the pertinent art will recognize that other integrated circuits may be used without departing from the scope and spirit of the present invention.

Figure 5:
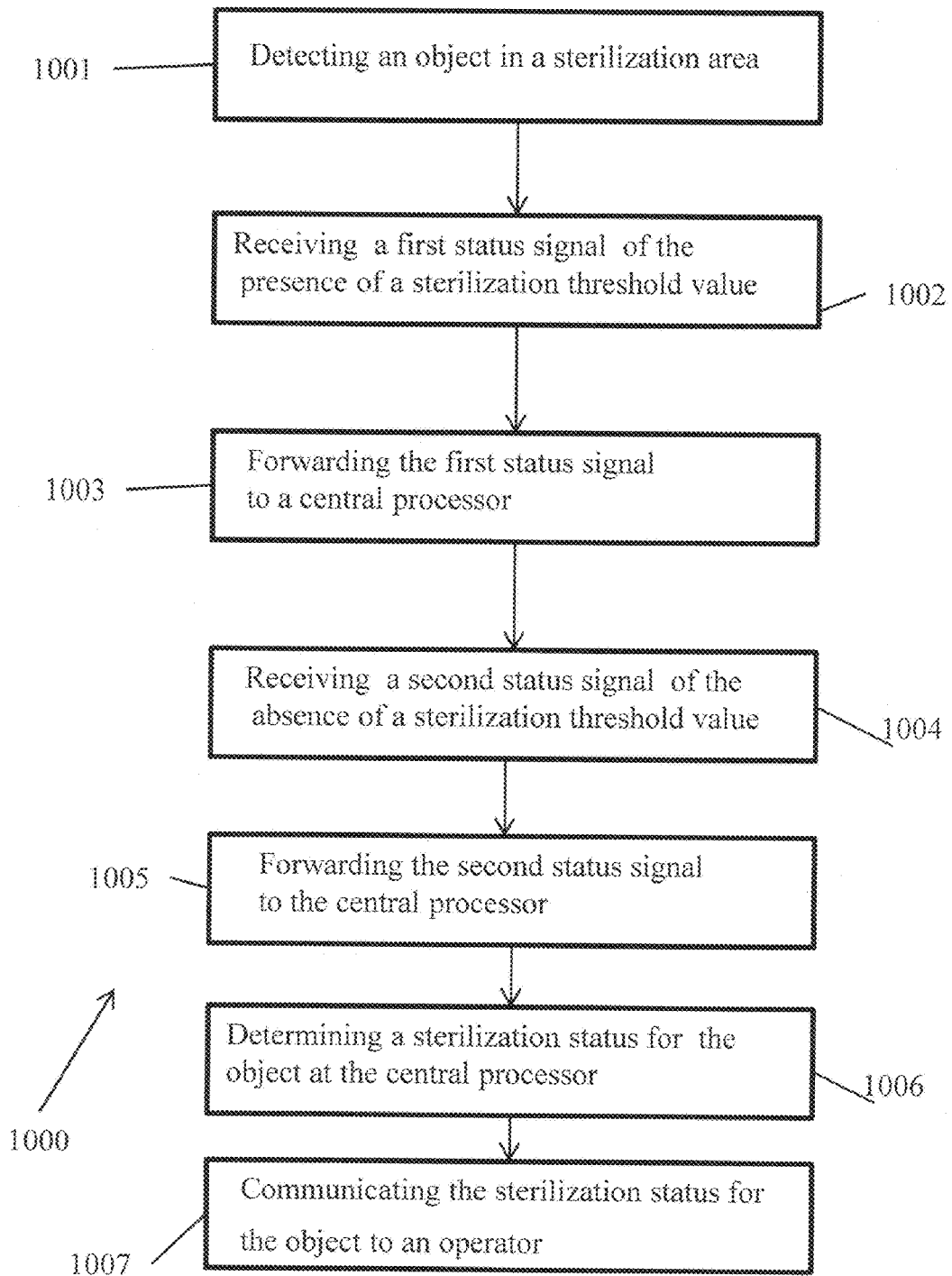
FIG. 5 is a flow chart of a general method for real-time location monitoring of a sterilizable object.

A method 1000 for real-time location monitoring of a sterilizable object is illustrated in FIG. 5. At block 1001, a sterilizable object 100 having a tag 60 is tracked in a sterilization area of the facility 70 by at least one sensor 55. The sterilization area is where any or all of cleaning, disinfecting and/or sterilizing a sterilizable object 100 is performed within the facility 70. At block 1002, a first status signal is received by at least one sensor 55 from the tag 60 indicating the presence of a sterilization threshold value. The presence of the sterilization threshold value is indicative of the beginning of a sterilization procedure for the sterilizable object 100. At block 1003, the first status signal is forwarded to a central processor. The first status signal preferably comprises data including time, date, location, object identification, and the sterilization threshold value detected. At block 1004, a second status signal is received by at least one sensor 55 from the tag 60 indicating the absence of the sterilization threshold value. At block 1005, the second status signal is forwarded to the central processor. The absence of the sterilization threshold value is indicative of the end of the sterilization procedure for the sterilizable object 100. The second status signal preferably comprises data including time, date, location, object identification, and a termination of sterilization threshold value message. At block 1006, the central processor determines a sterilization status for the sterilizable object based on at least the first status signal and the second status signal. The central processor calculates the time that the sterilizable object 100 was exposed to the sterilization event and the intensity of the exposure. The calculated values are compared to stored data for prescribed sterilization values to determine if the sterilizable object was properly sterilized. At block 1007, the sterilization status is communicated to an operator. The communication informs the operator if the sterilization procedure was complete or incomplete. The sterilization events are preferably a known sequence of at least one of a series of predefined temperature, a series of predefined locations, an ordered series of predefined locations the absence of a series of predefined temperatures and the absence of predefined locations.

Figure 4C:
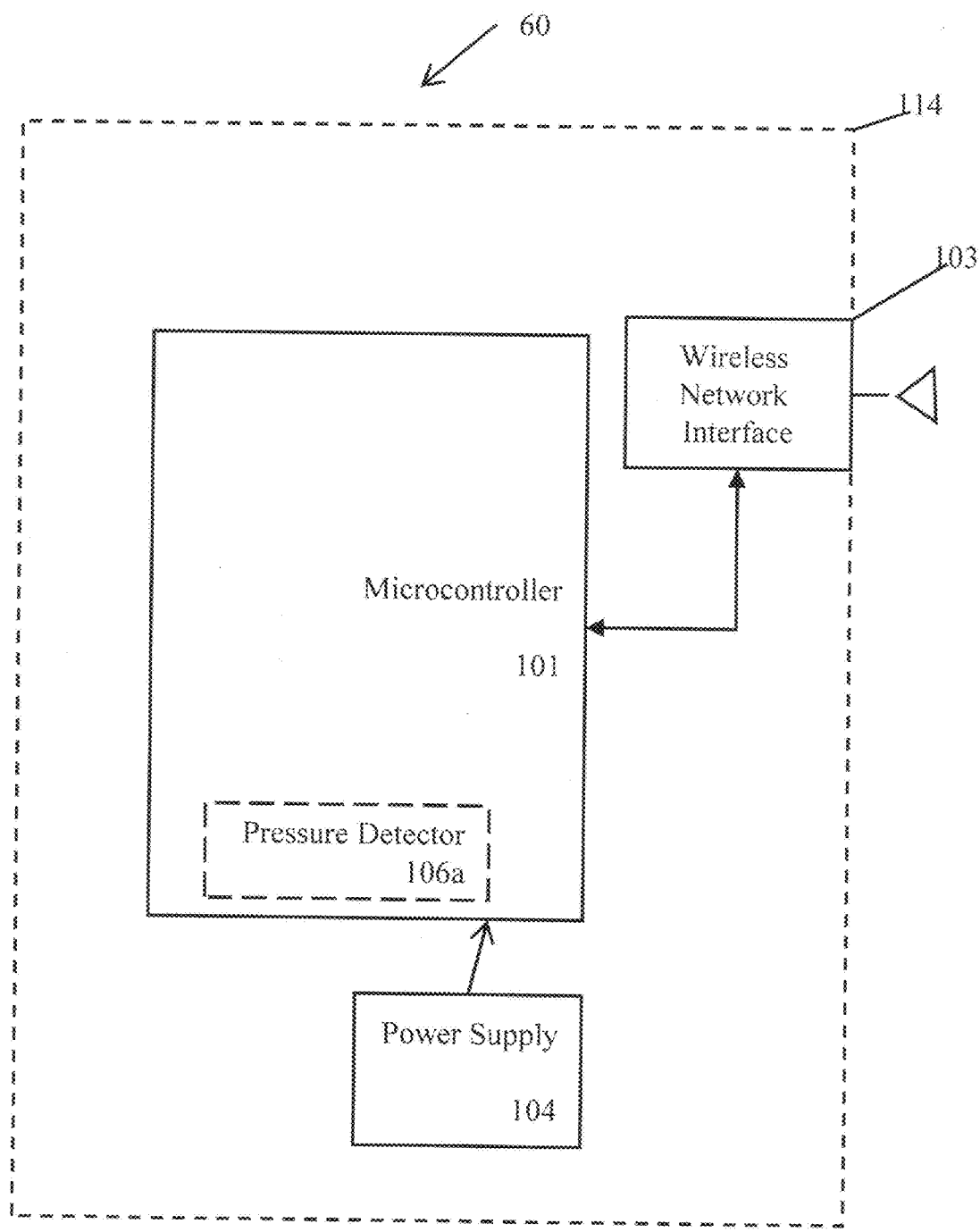
FIG. 4C is a block diagram of an alternative embodiment of a tag with an integrated circuit having a pressure detector.

As shown in FIG. 4C, the sensor is a pressure detector 106a. One particular type of pressure sensor is a piezoresistive OEM pressure transducer. The pressure detector 106a detects a change in environmental pressure, which is a sterilization event transmitted by the microcontroller 101 to the wireless network interface 103 for broadcast to the network sensors 55 for eventual communication to the server 65. Preferably, pressure is utilized with steam sterilization. One such apparatus for sterilizing an object is a pressure cooker, which can provide the necessary steam and pressure for sterilization. A pressure of 1.036 Bar above atmospheric pressure is a preferred minimum pressure value for the threshold value.

Figure 5A:
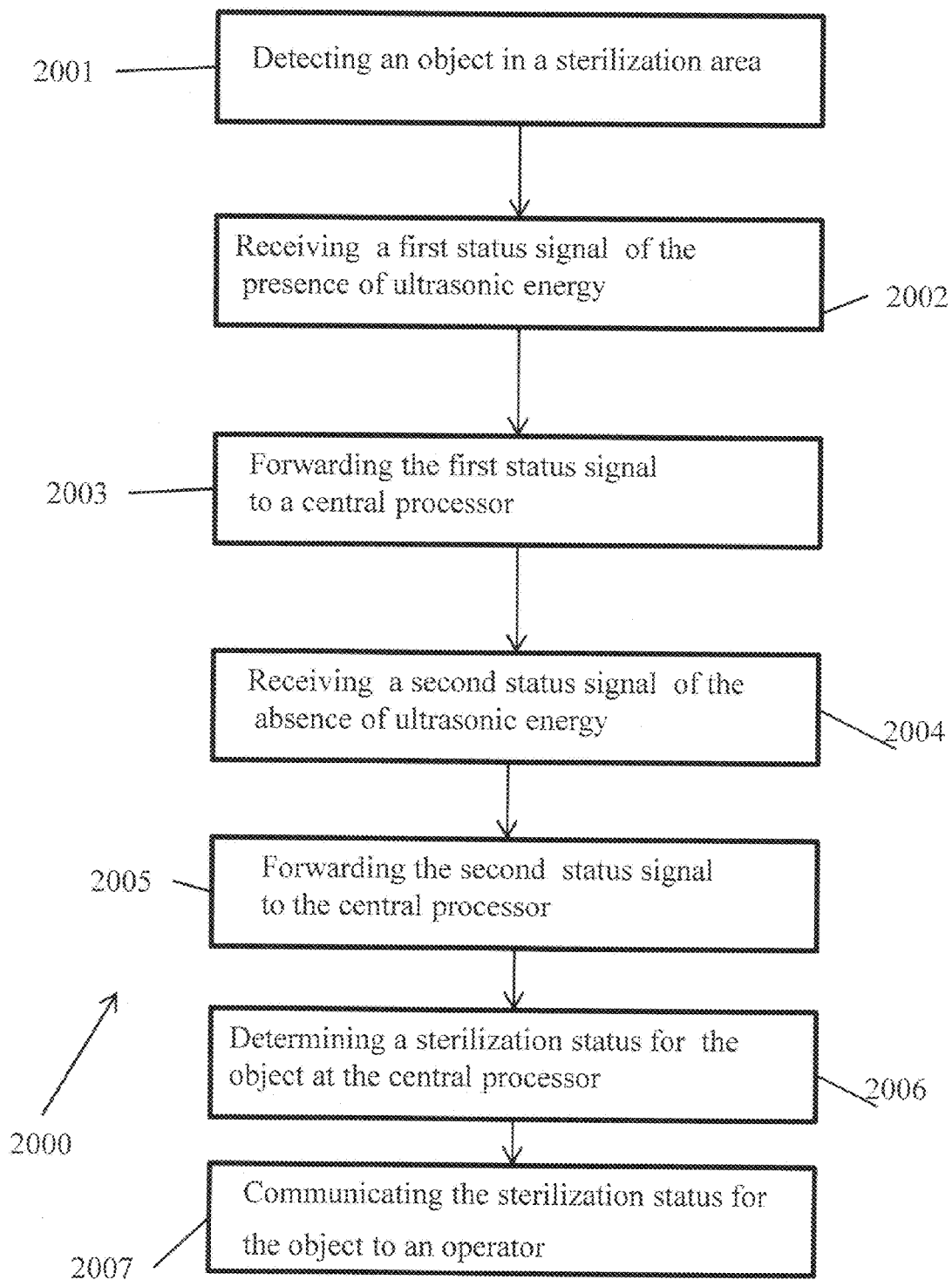
FIG. 5A is a flow chart of a specific method for real-time location monitoring of a sterilizable object utilizing an ultrasonic energy sterilization procedure.
Figure 5B:
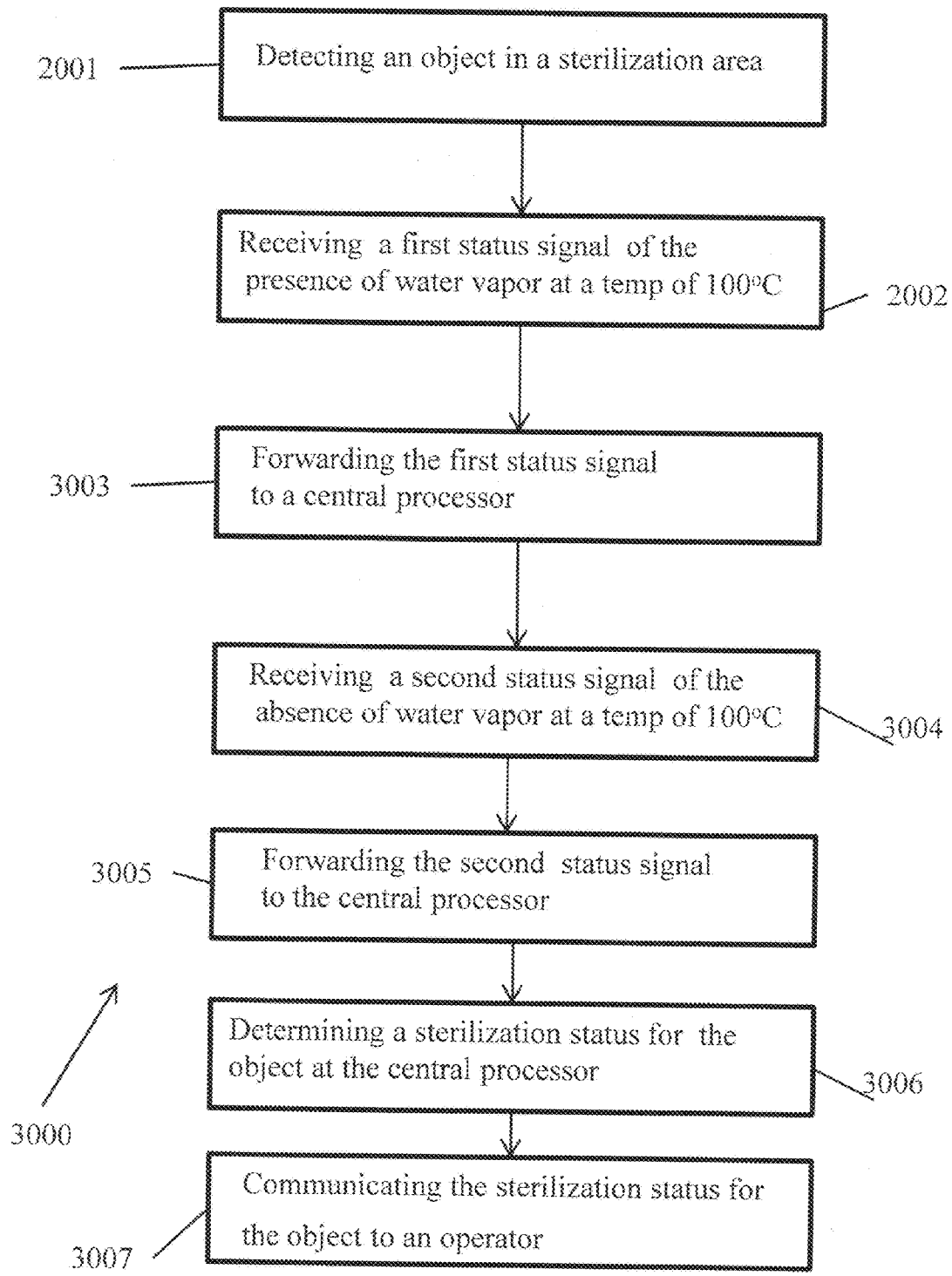
FIG. 5B is a flow chart of a specific method for real-time location monitoring of a sterilizable object utilizing a steam sterilization procedure.
Figure 5C:
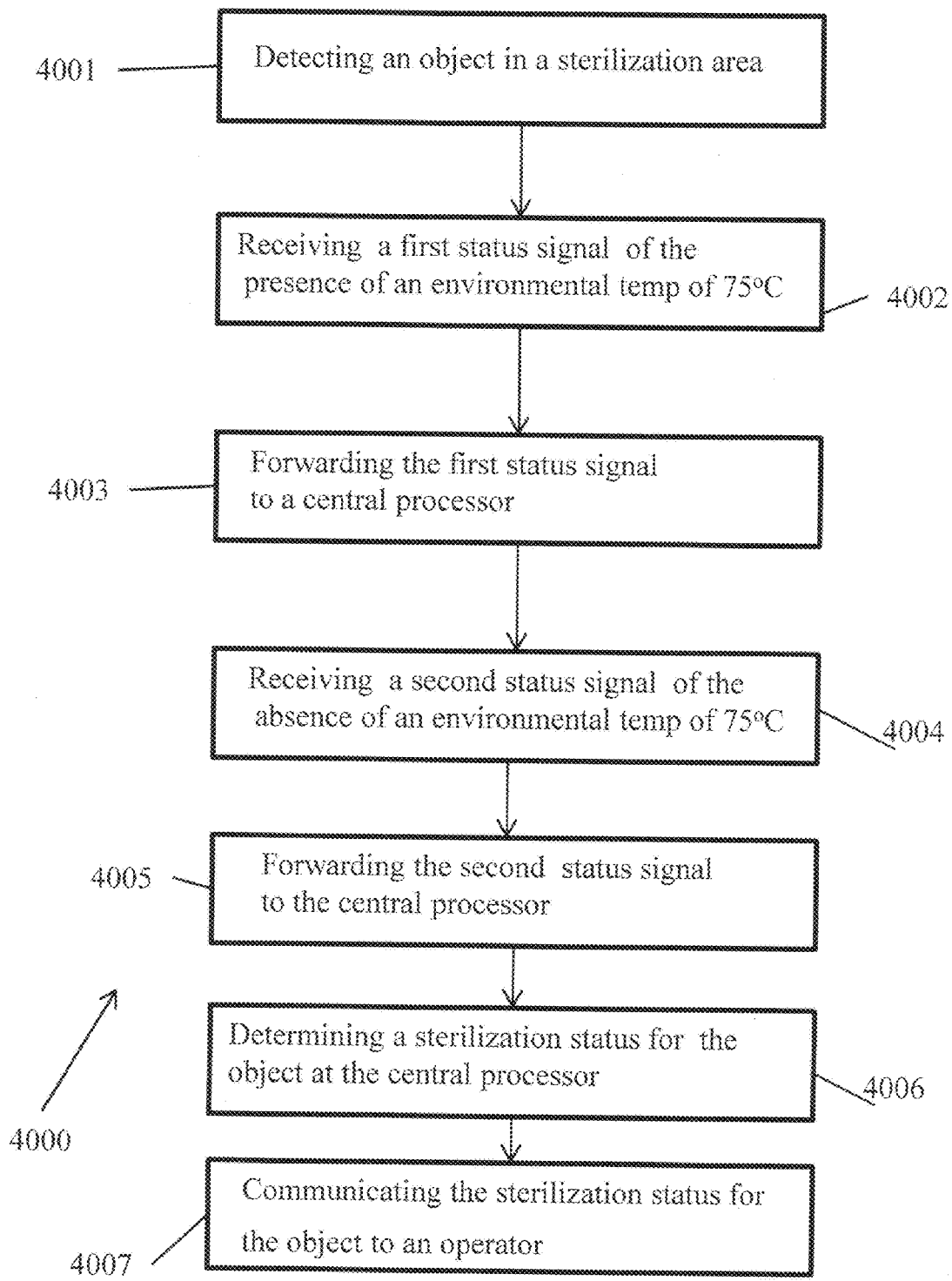
FIG. 5C is a flow chart of a specific method for real-time location monitoring of a sterilizable object utilizing a high temperature sterilization procedure.
Figure 5D:
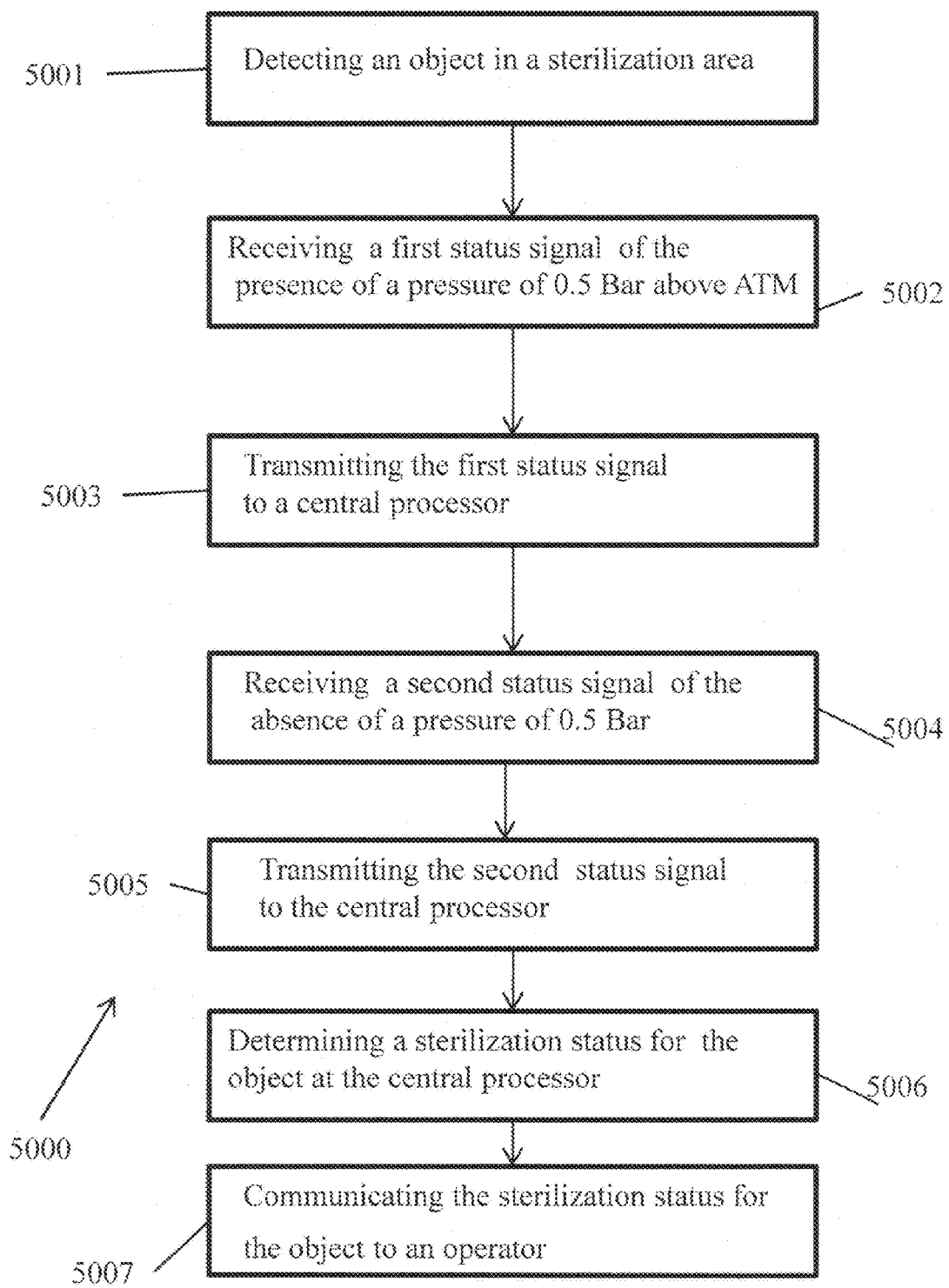
FIG. 5D is a flow chart of a specific method for real-time location monitoring of a sterilizable object utilizing a pressurized environment sterilization procedure.

A specific method 5000 for real-time location monitoring of a sterilizable object is illustrated in FIG. 5D. At block 5001, a sterilizable object 100 having a tag 60 is tracked in a sterilization area of the facility 70 by at least one sensor 55 for sterilization utilizing a pressurized environment. At block 5002, a first status signal is received by at least one sensor 55 from the tag 60 indicating the presence of pressurized environment of at least 0.5 Bar above a standard atmospheric pressure, which is the sterilization threshold value for a sterilization pressure utilizing a pressurized environment. The presence of the sterilization threshold value is indicative of the beginning of a sterilization procedure for the sterilizable object 100. At block 5003, the first status signal is forwarded to a central processor. The first status signal preferably comprises data including time, date, location, object identification, and the sterilization threshold value detected. At block 5004, a second status signal is received by at least one sensor 55 from the tag 60 indicating the absence of the sterilization threshold value. At block 5005, the second status signal is forwarded to the central processor. The absence of the sterilization threshold value is preferably indicative of the end of the sterilization procedure for the sterilizable object 100. Alternatively, the absence of the sterilization threshold value is indicative of a state change in a workflow of the sterilization procedure for the sterilizable object 100. The second status signal preferably comprises data including time, date, location, object identification, association with another object, and/or a termination of sterilization threshold value message. At block 5006, the central processor determines a sterilization status for the sterilizable object based on at least the first status signal and the second status signal. The central processor calculates the time that the sterilizable object 100 was exposed to the sterilization event and the intensity of the exposure. A person skilled in the pertinent art will recognize that that the afore-mentioned calculations could be performed locally on the device or in a distributed manner by a group of devices within a network. The calculated values are compared to stored data for prescribed sterilization values to determine if the sterilizable object was properly sterilized utilizing a sterile process. For example, one sterilization procedure requires steam at a temperature of 121° C. applied at a pressure of 1.036 Bar above atmospheric pressure for twenty minutes for effectiveness. Another sterilization procedure requires steam at a temperature of 134° C. applied at a pressure of 2.026 Bar above atmospheric pressure for four minutes for effectiveness. At block 5007, the sterilization status is communicated to an operator. The communication informs the operator if the sterilization procedure was complete or incomplete.

Figure 4D:
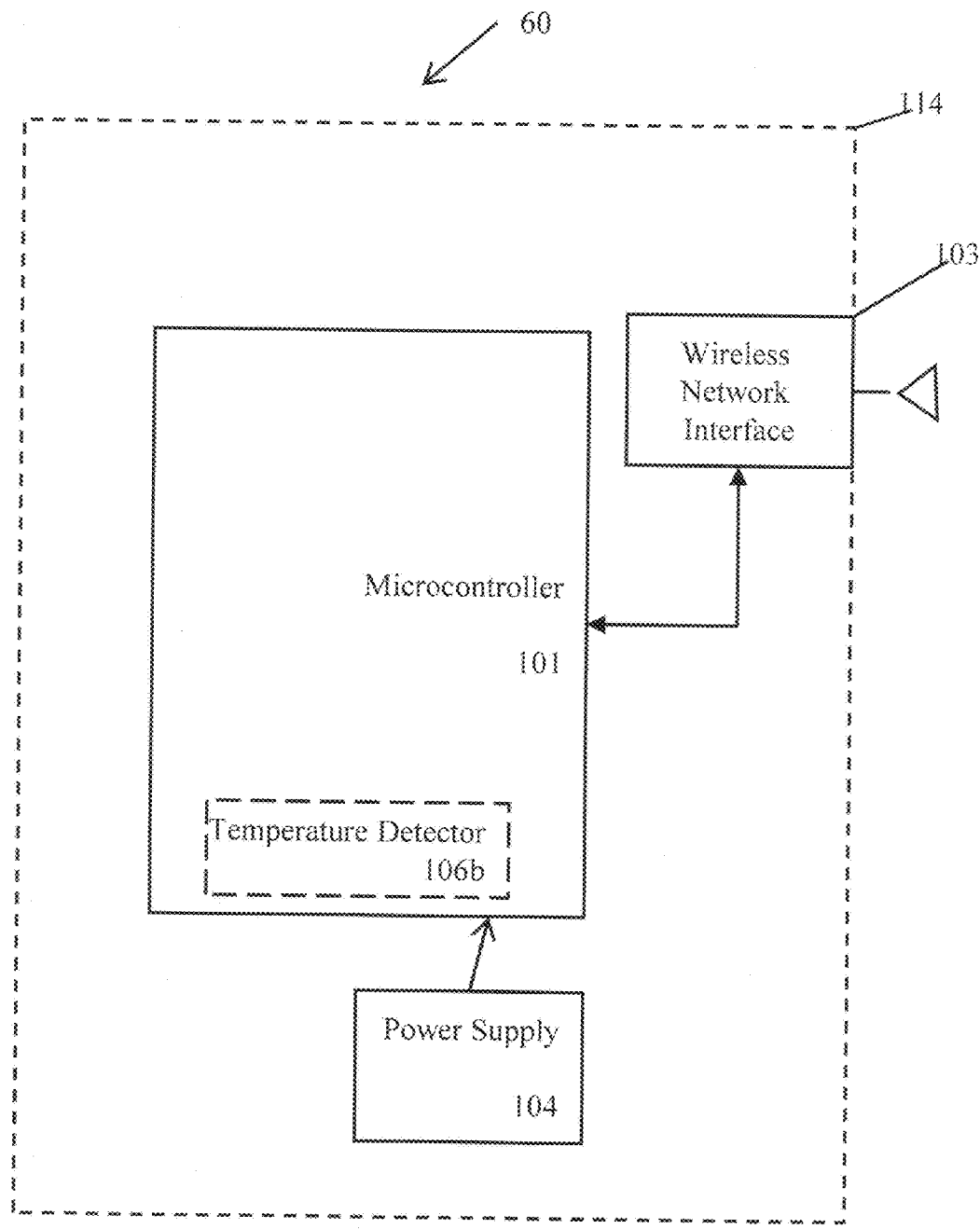
FIG. 4D is a block diagram of an alternative embodiment of a tag with an integrated circuit having a temperature detector.

As shown in FIG. 4D, in alternative embodiment of the tag 60 the sensor is a temperature detector 106b. The temperature detector 106b detects a change in the environmental temperature, which is a sterilization event transmitted by the microcontroller 101 to the wireless network interface 103 for broadcast to the network sensors 55 for eventual communication to the server 65.

Another specific method 4000 for real-time location monitoring of a sterilizable object is illustrated in FIG. 5C. At block 4001, a sterilizable object 100 having a tag 60 is tracked in a sterilization area of the facility 70 by at least one sensor 55 for sterilization utilizing a high temperature environment. At block 4002, a first status signal is received by at least one sensor 55 from the tag 60 indicating the presence of high temperature environment of at least 75° C., which is the sterilization threshold value for a sterilization pressure utilizing a high temperature environment. The presence of the sterilization threshold value is indicative of the beginning of a sterilization procedure for the sterilizable object 100. At block 4003, the first status signal is forwarded to a central processor. The first status signal preferably comprises data including time, date, location, object identification, and the sterilization threshold value detected. At block 4004, a second status signal is received by at least one sensor 55 from the tag 60 indicating the absence of the sterilization threshold value. At block 4005, the second status signal is forwarded to the central processor. The absence of the sterilization threshold value is preferably indicative of the end of the sterilization procedure for the sterilizable object 100. Alternatively, the absence of the sterilization threshold value is indicative of a state change in a workflow of the sterilization procedure for the sterilizable object 100. The second status signal preferably comprises data including time, date, location, object identification, association with another object, and/or a termination of sterilization threshold value message. At block 4006, the central processor determines a sterilization status for the sterilizable object based on at least the first status signal and the second status signal. The central processor calculates the time that the sterilizable object 100 was exposed to the sterilization event and the intensity of the exposure. The calculated values are compared to stored data for prescribed sterilization values to determine if the sterilizable object was properly sterilized utilizing a high temperature environment. For example, one sterilization procedure for dry heat sterilization requires a temperature of 180° C. for thirty minutes for effectiveness. Another sterilization procedure for dry heat sterilization requires a temperature of 141° C. for three hours for effectiveness. At block 4007, the sterilization status is communicated to an operator. The communication informs the operator if the sterilization procedure was complete or incomplete.

Figure 4E:
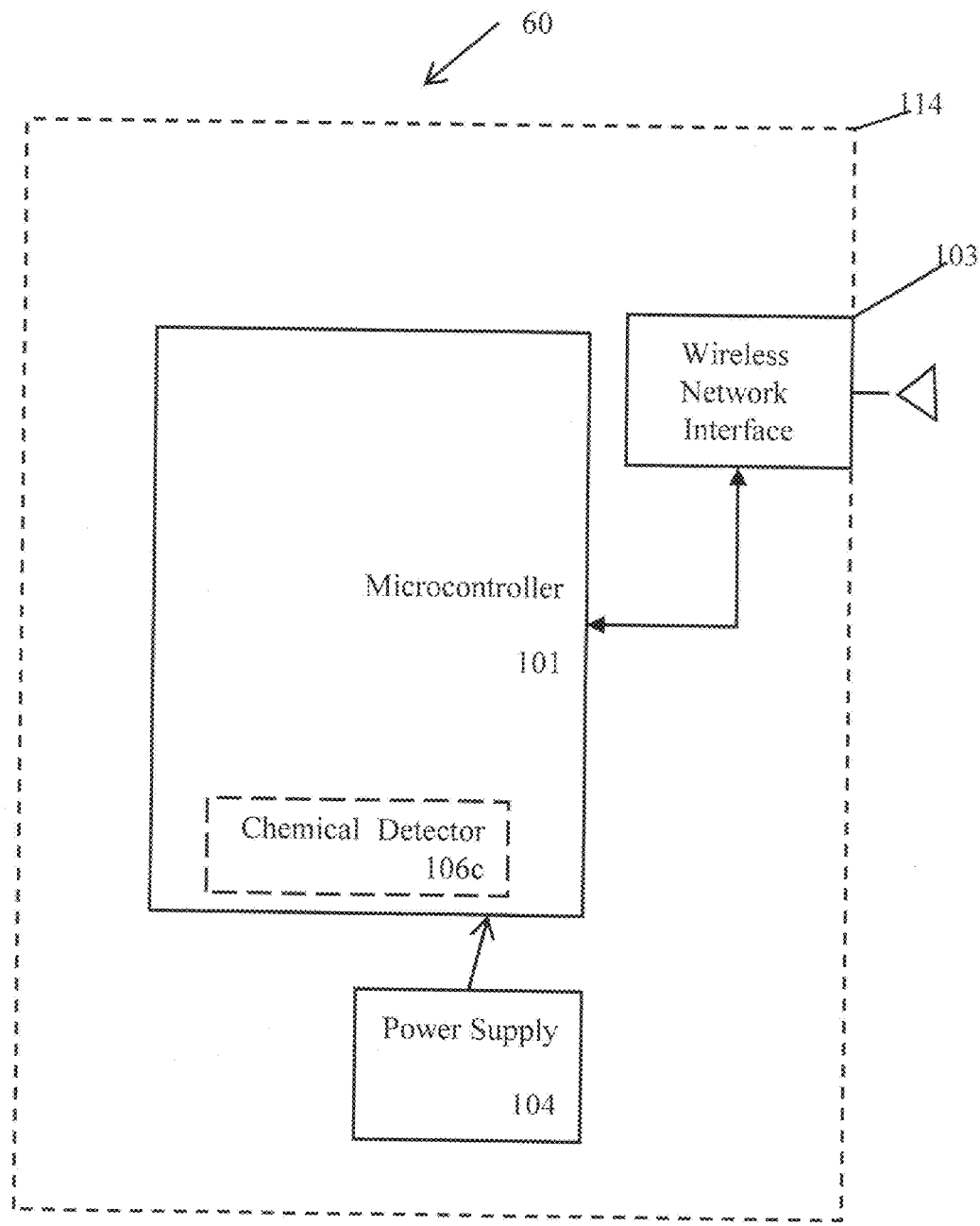
FIG. 4E is a block diagram of an alternative embodiment of a tag with an integrated circuit having a chemical detector.

As shown in FIG. 4E, in alternative embodiment of the tag 60 the sensor is a chemical detector 106c. The chemical detector 106c detects a pH change or the presence of a chemical, which is a sterilization event transmitted by the microcontroller 101 to the wireless network interface 103 for broadcast to the network sensors 55 for eventual communication to the server 65.

Figure 5E:
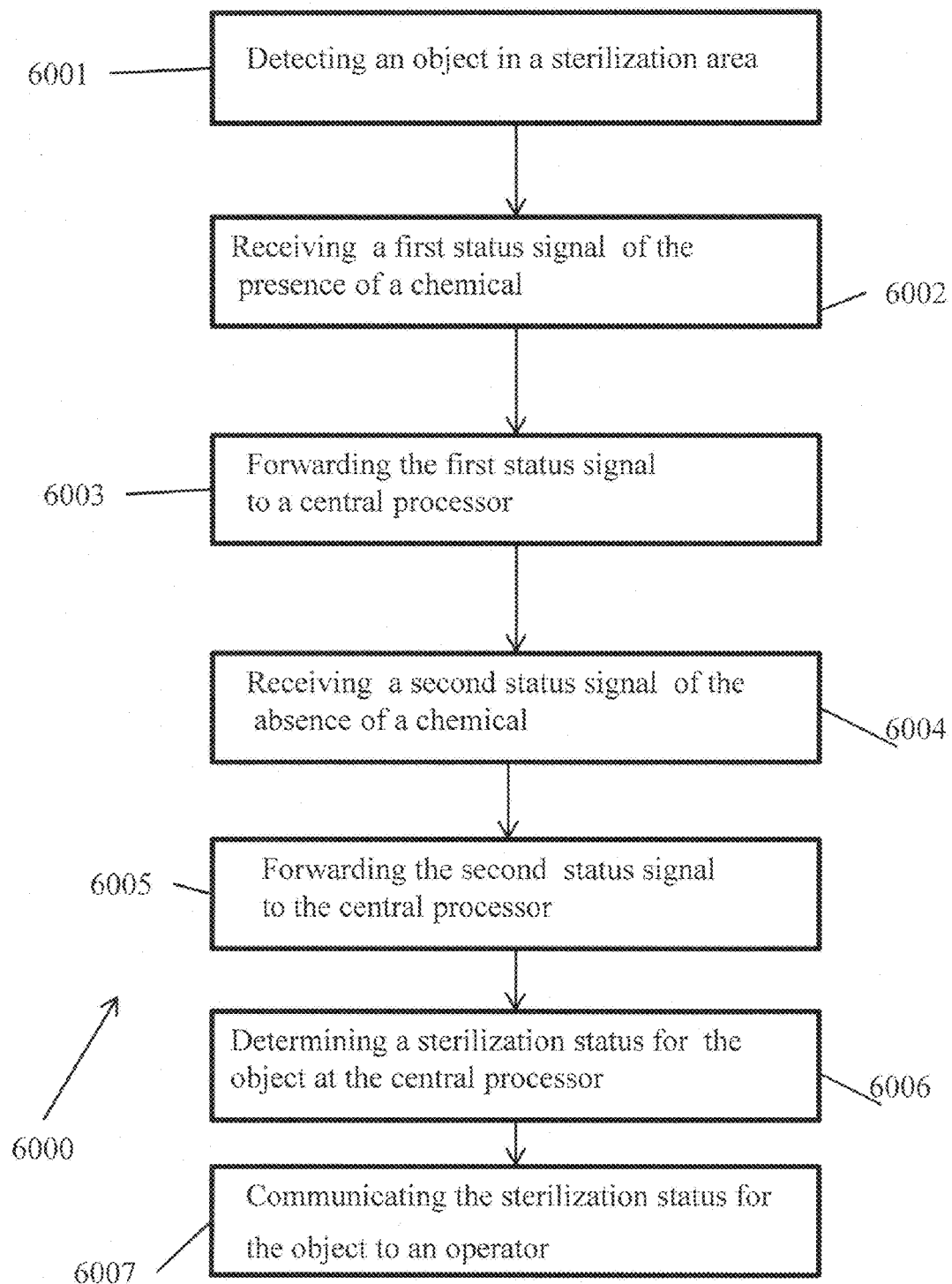
FIG. 5E is a flow chart of a specific method for real-time location monitoring of a sterilizable object utilizing a chemical sterilant sterilization procedure.

Another specific method 6000 for real-time location monitoring of a sterilizable object is illustrated in FIG. 5E. At block 6001, a sterilizable object 100 having a tag 60 is tracked in a sterilization area of the facility 70 by at least one sensor 55 for sterilization utilizing a chemical sterilant. Chemical sterilants are primarily used for heat-labile sterilizable objects 100. The sterilizable objects are sterilized by soaking the sterilizable object 100 in a chemical solution followed by rinsing in sterile water. At block 6002, a first status signal is received by at least one sensor 55 from the tag 60 indicating the presence of a chemical sterilant, which is the sterilization threshold value for a sterilization pressure utilizing a chemical sterilant. The presence of the sterilization threshold value is indicative of the beginning of a sterilization procedure for the sterilizable object 100. At block 6003, the first status signal is forwarded to a central processor. The first status signal preferably comprises data including time, date, location, object identification, and the sterilization threshold value detected. At block 6004, a second status signal is received by at least one sensor 55 from the tag 60 indicating the absence of the sterilization threshold value. At block 6005, the second status signal is forwarded to the central processor. The absence of the sterilization threshold value is preferably indicative of the end of the sterilization procedure for the sterilizable object 100. Alternatively, the absence of the sterilization threshold value is indicative of a state change in a workflow of the sterilization procedure for the sterilizable object 100. The second status signal preferably comprises data including time, date, location, object identification, association with another object, and/or a termination of sterilization threshold value message. At block 6006, the central processor determines a sterilization status for the sterilizable object based on at least the first status signal and the second status signal. The central processor calculates the time that the sterilizable object 100 was exposed to the sterilization event and the intensity of the exposure. The calculated values are compared to stored data for prescribed sterilization values to determine if the sterilizable object was properly sterilized utilizing a chemical sterilant. For example, one chemical sterilant sterilizing procedure requires immersion in a 2% glutaraldehyde solution for twenty minutes for effectiveness. Another chemical sterilant sterilizing procedure requires immersion in a 0.35% peracetic solution for ten minutes for effectiveness. Another chemical sterilant sterilizing procedure requires immersion in a 7.5% hydrogen peroxide solution for twenty minutes for effectiveness. At block 6007, the sterilization status is communicated to an operator. The communication informs the operator if the sterilization procedure was complete or incomplete.

Figure 4F:
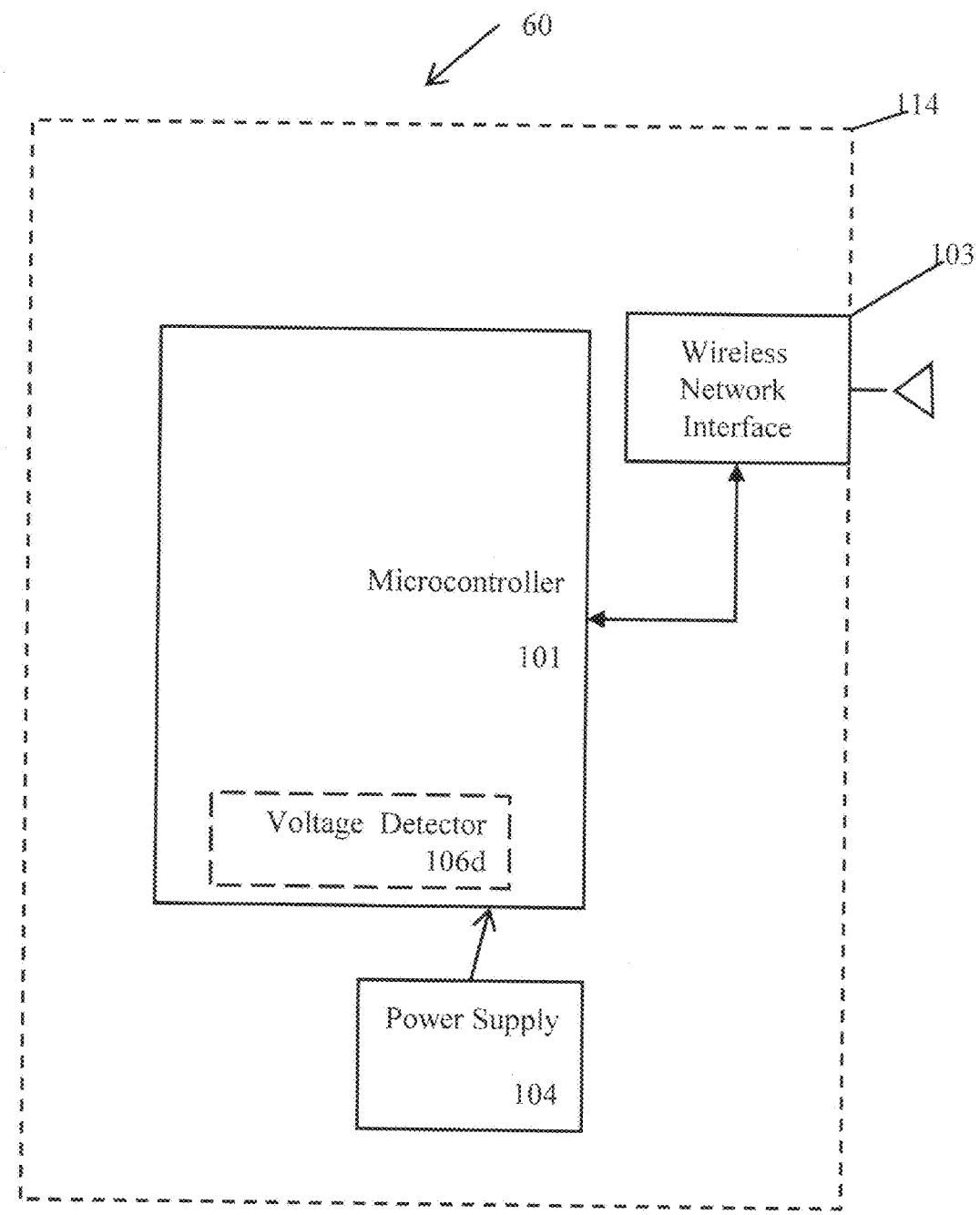
FIG. 4F is a block diagram of an alternative embodiment of a tag with an integrated circuit having a voltage detector.

As shown in FIG. 4F, in alternative embodiment of the tag 60 the sensor is a voltage detector 106d. The voltage detector 106d detects a change in the voltage of the tag 60, which is a sterilization event transmitted by the microcontroller 101 to the wireless network interface 103 for broadcast to the network sensors 55 for eventual communication to the server 65.

Figure 4G:
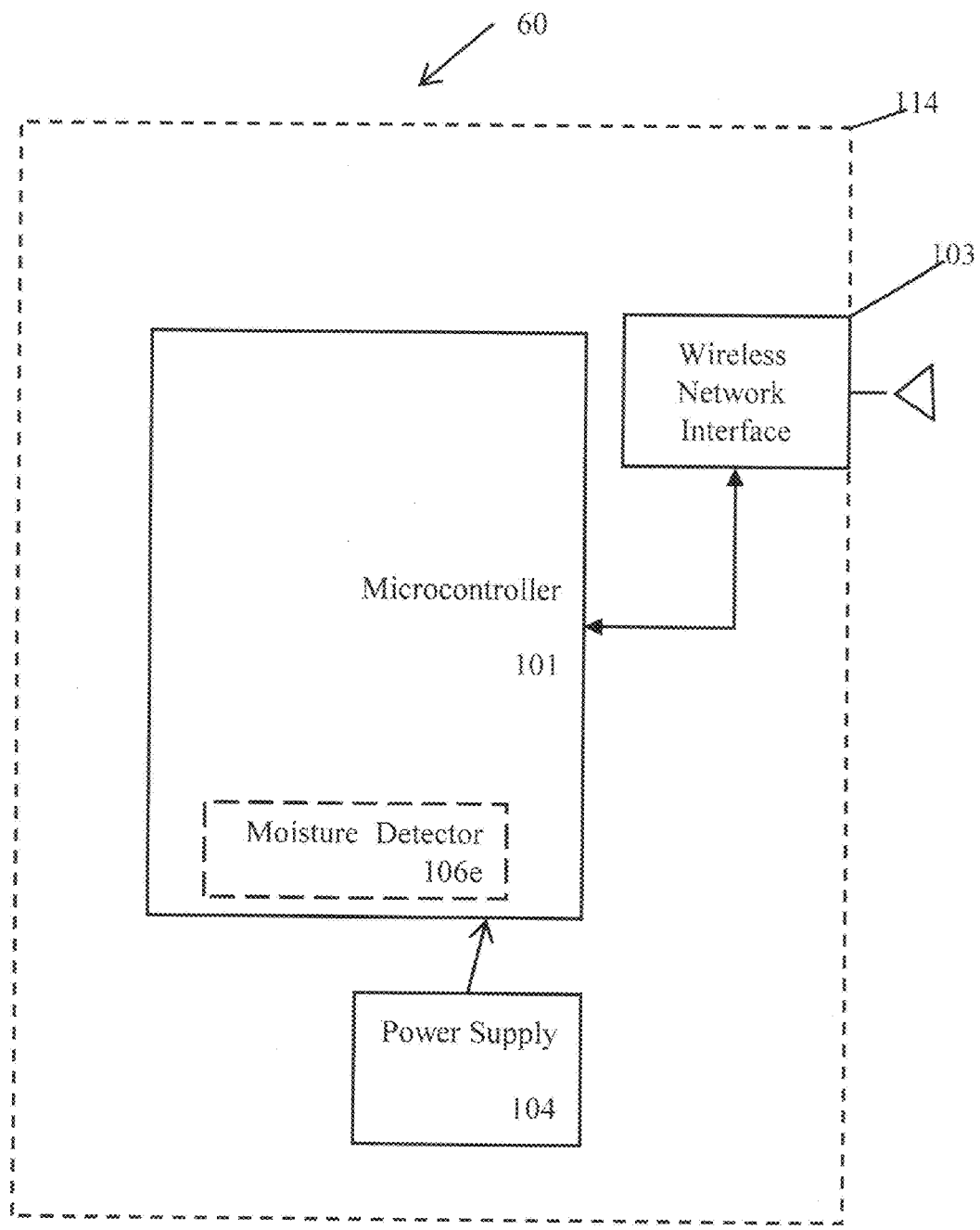
FIG. 4G is a block diagram of an alternative embodiment of a tag with an integrated circuit having a moisture detector.

As shown in FIG. 4G, in alternative embodiment of the tag 60 the sensor is a moisture detector 106e. The moisture detector 106e detects the presence of moisture, which is a sterilization event transmitted by the microcontroller 101 to the wireless network interface 103 for broadcast to the network sensors 55 for eventual communication to the server 65.

Figure 5F:
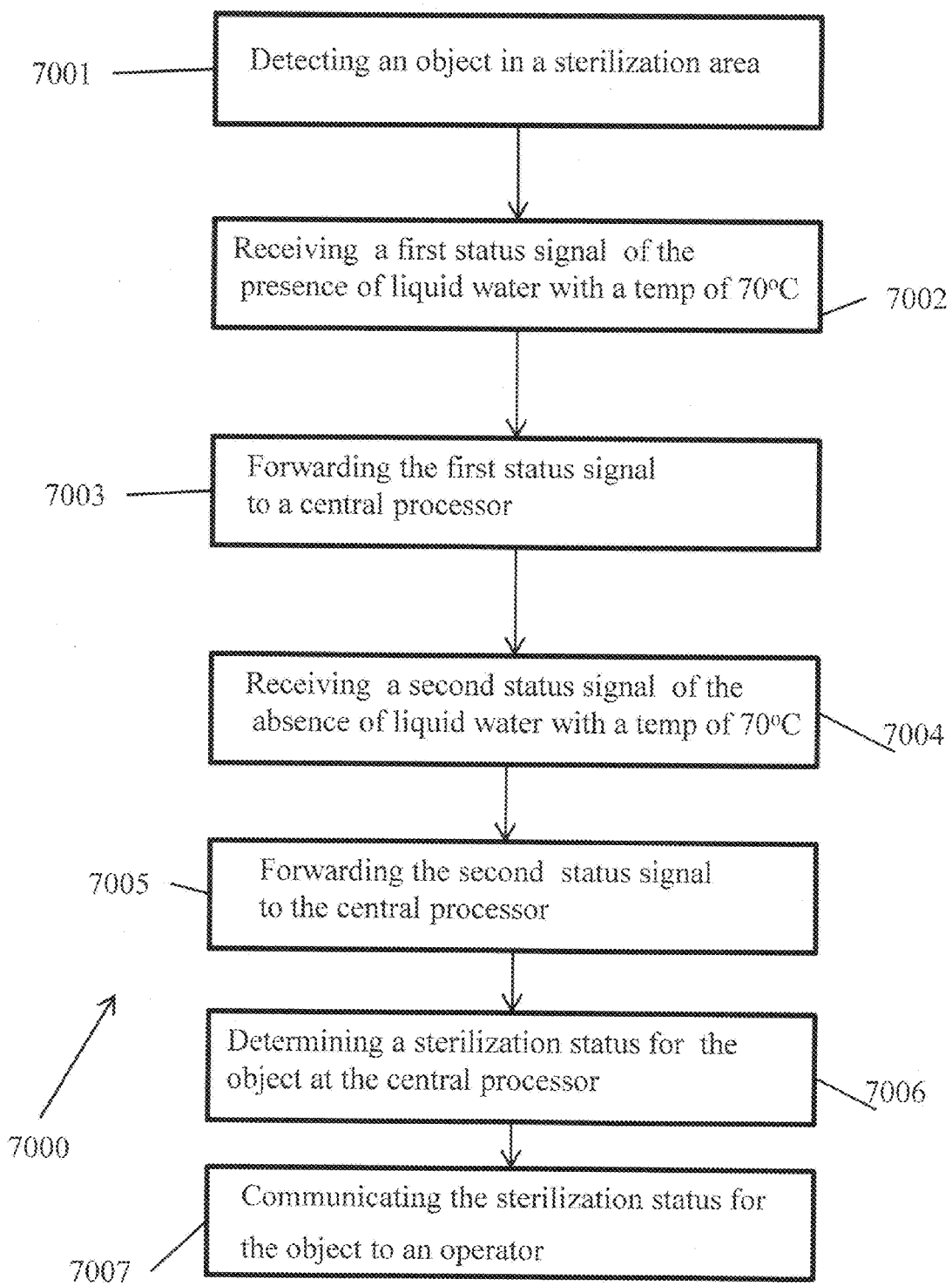
FIG. 5F is a flow chart of a specific method for real-time location monitoring of a sterilizable object utilizing a hot water sterilization procedure.

Another specific method 7000 for real-time location monitoring of a sterilizable object is illustrated in FIG. 5F. At block 7001, a sterilizable object 100 having a tag 60 is tracked in a sterilization area of the facility 70 by at least one sensor 55 for sterilization utilizing a hot water environment. At block 7002, a first status signal is received by at least one sensor 55 from the tag 60 indicating the presence of hot water environment of at least 70° C., which is the sterilization threshold value for a sterilization pressure utilizing a hot water environment. The presence of the sterilization threshold value is indicative of the beginning of a sterilization procedure for the sterilizable object 100. At block 7003, the first status signal is forwarded to a central processor. The first status signal preferably comprises data including time, date, location, object identification, and the sterilization threshold value detected. At block 7004, a second status signal is received by at least one sensor 55 from the tag 60 indicating the absence of the sterilization threshold value. At block 7005, the second status signal is forwarded to the central processor. The absence of the sterilization threshold value is preferably indicative of the end of the sterilization procedure for the sterilizable object 100. Alternatively, the absence of the sterilization threshold value is indicative of a state change in a workflow of the sterilization procedure for the sterilizable object 100. The second status signal preferably comprises data including time, date, location, object identification, association with another object, and/or a termination of sterilization threshold value message. At block 7006, the central processor determines a sterilization status for the sterilizable object based on at least the first status signal and the second status signal. The central processor calculates the time that the sterilizable object 100 was exposed to the sterilization event and the intensity of the exposure. The calculated values are compared to stored data for prescribed sterilization values to determine if the sterilizable object was properly sterilized utilizing a high temperature environment. For example, one sterilization procedure for hot water sterilization requires a temperature of 70° C. for two minutes followed by a hot water rinse at 90° C. for ten seconds and then drying at 75° C. for effectiveness. At block 7007, the sterilization status is communicated to an operator. The communication informs the operator if the sterilization procedure was complete or incomplete.

Another specific method 3000 for real-time location monitoring of a sterilizable object is illustrated in FIG. 5B. At block 3001, a sterilizable object 100 having a tag 60 is tracked in a sterilization area of the facility 70 by at least one sensor 55 for sterilization utilizing a steam environment. At block 3002, a first status signal is received by at least one sensor 55 from the tag 60 indicating the presence of a steam environment of at least 100° C., which is the sterilization threshold value for a sterilization pressure utilizing a steam environment. The presence of the sterilization threshold value is indicative of the beginning of a sterilization procedure for the sterilizable object 100. At block 3003, the first status signal is forwarded to a central processor. The first status signal preferably comprises data including time, date, location, object identification, and the sterilization threshold value detected. At block 3004, a second status signal is received by at least one sensor 55 from the tag 60 indicating the absence of the sterilization threshold value. At block 3005, the second status signal is forwarded to the central processor. The absence of the sterilization threshold value is preferably indicative of the end of the sterilization procedure for the sterilizable object 100. Alternatively, the absence of the sterilization threshold value is indicative of a state change in a workflow of the sterilization procedure for the sterilizable object 100. The second status signal preferably comprises data including time, date, location, object identification, association with another object, and/or a termination of sterilization threshold value message. At block 3006, the central processor determines a sterilization status for the sterilizable object based on at least the first status signal and the second status signal. The central processor calculates the time that the sterilizable object 100 was exposed to the sterilization event and the intensity of the exposure. The calculated values are compared to stored data for prescribed sterilization values to determine if the sterilizable object was properly sterilized utilizing a high temperature environment. For example, one sterilization procedure for steam sterilization requires steam at a temperature of 121° C. for thirty minutes for effectiveness. At block 3007, the sterilization status is communicated to an operator. The communication informs the operator if the sterilization procedure was complete or incomplete.

Figure 4H:
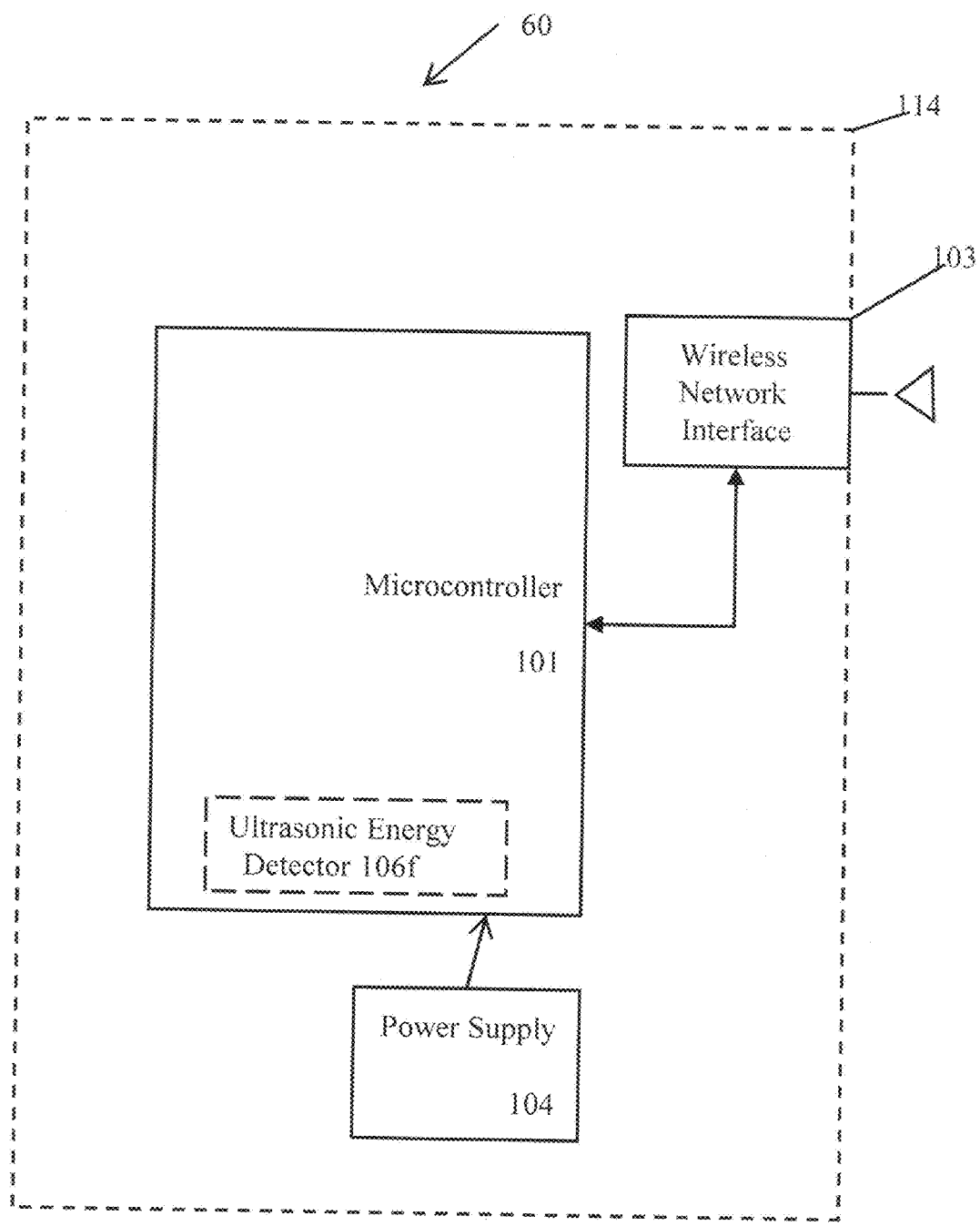
FIG. 4H is a block diagram of an alternative embodiment of a tag with an integrated circuit having an ultrasonic energy detector.

As shown in FIG. 4H, in alternative embodiment of the tag 60 the sensor is an ultrasonic energy detector 106f. The ultrasonic energy detector 106f detects the presence of ultrasonic energy, which is a sterilization event transmitted by the microcontroller 101 to the wireless network interface 103 for broadcast to the network sensors 55 for eventual communication to the server 65.

Another specific method 2000 for real-time location monitoring of a sterilizable object is illustrated in FIG. 5A. At block 2001, a sterilizable object 100 having a tag 60 is tracked in a sterilization area of the facility 70 by at least one sensor 55 for sterilization utilizing ultrasonic energy. At block 2002, a first status signal is received by at least one sensor 55 from the tag 60 indicating the presence of ultrasonic energy, greater than 20,000 Hertz, which is the sterilization threshold value for a sterilization pressure utilizing ultrasonic energy. The presence of the sterilization threshold value is indicative of the beginning of a sterilization procedure for the sterilizable object 100. At block 2003, the first status signal is forwarded to a central processor. The first status signal preferably comprises data including time, date, location, object identification, and the sterilization threshold value detected. At block 2004, a second status signal is received by at least one sensor 55 from the tag 60 indicating the absence of the sterilization threshold value. At block 2005, the second status signal is forwarded to the central processor. The absence of the sterilization threshold value is preferably indicative of the end of the sterilization procedure for the sterilizable object 100. Alternatively, the absence of the sterilization threshold value is indicative of a state change in a workflow of the sterilization procedure for the sterilizable object 100. The second status signal preferably comprises data including time, date, location, object identification, association with another object, and/or a termination of sterilization threshold value message. At block 2006, the central processor determines a sterilization status for the sterilizable object based on at least the first status signal and the second status signal. The central processor calculates the time that the sterilizable object 100 was exposed to the sterilization event and the intensity of the exposure. The calculated values are compared to stored data for prescribed sterilization values to determine if the sterilizable object was properly sterilized utilizing ultrasonic energy. The communication informs the operator if the sterilization procedure was complete or incomplete.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention:

1. A method for real-time location monitoring of a sterilizable object within an indoor facility, the method comprising:

tracking a real-time location of a sterilizable object within the indoor facility utilizing a mesh network formed of a plurality of sensors and at least one access bridge positioned within the indoor facility, the sterilizable object associated with a tag that transmits a continuous periodic radiofrequency signal;

receiving at least one of the plurality of sensors a tracking signal from the tag that the sterilizable object is located in a sterilization area;

receiving at least one of the plurality of sensors a first status signal from the tag that a sterilization threshold value for a sterilization event is present, the sterilization threshold value detected by a sensor of the tag;

transmitting the first status signal from the at least one of the plurality of sensors through the mesh network to a remote server;

receiving at least one of the plurality of sensors a second status signal from the tag that the sterilization threshold value for a sterilization event is absent;

transmitting the second status signal from the at least one of the plurality of sensors to a remote server;

determining a sterilization status for the sterilizable object at the remote server based on at least the first status signal and the second status signal; and communicating the sterilization status for the sterilizable object to an operator;

wherein the sterilization event is one of ultrasonic energy sterilization, steam sterilization, heat sterilization, pressure sterilization, chemical sterilization and hot water sterilization, and wherein an ultrasonic energy sterilization has a sterilization threshold value of a detection of a pre-established amount of ultrasonic energy, a steam sterilization has a sterilization threshold value of a detection of water vapor at a temperature of at least 100° C., a heat sterilization has a sterilization threshold value of a detection of a temperature of at least 150° C., a pressure sterilization has a sterilization threshold value of a detection of a pressure of at least 1.036 Bar above atmospheric pressure, a chemical sterilization has a sterilization threshold value of a detection of hydrogen peroxide in a concentration amount of at least 6%, and a hot water sterilization has a sterilization threshold value of a detection of liquid water at a temperature of at least 70° C.

2. The method according to claim 1 wherein the sterilization status is a message that the sterilization was complete.

3. The method according to claim 1 wherein the sterilization status is a message that the sterilization was incomplete.

4. A method for real-time location monitoring of a sterilizable object within an indoor facility, the method comprising:

tracking a real-time location of a sterilizable object within the indoor facility utilizing a mesh network formed of a plurality of sensors and at least one access bridge positioned within the indoor facility, the sterilizable object associated with a tag that transmits a continuous periodic radiofrequency signal;

receiving at least one of the plurality of sensors a tracking signal from the tag that the sterilizable object is located in a sterilization area;

receiving at least one of the plurality of sensors a first status signal from the tag that a sterilization threshold value for a sterilization event is present, the sterilization threshold value detected by a sensor of the tag;

transmitting the first status signal from the at least one of the plurality of sensors through the mesh network to a remote server;

receiving at least one of the plurality of sensors a second status signal from the tag that the sterilization threshold value for a sterilization event is absent;

transmitting the second status signal from the at least one of the plurality of sensors to a remote server;

determining a sterilization status for the sterilizable object at the remote server based on at least the first status signal and the second status signal; and communicating the sterilization status for the sterilizable object to an operator;

wherein the sterilization event is one of steam sterilization, heat sterilization and hot water sterilization, and a steam sterilization has a sterilization threshold value of a detection of a temperature of at least 100° C., a heat sterilization has a sterilization threshold value of a detection of a temperature of at least 150° C., and a hot water sterilization has a sterilization threshold value of a detection of a temperature of at least 70° C.

5. A system for real-time location monitoring of a sterilizable object within an indoor facility, the system comprising:

a tracking tag attached to a sterilizable object, the tracking tag comprising a sealed housing, a sensor for detecting a sterilization event, a radiofrequency transceiver for transmitting a continuous periodic signal and data concerning the sterilization event;

a mesh network comprising a plurality of network sensors and at least one access bridge, each of the plurality of network sensors and the at least one access bridge positioned within the indoor facility, each of the plurality of network sensors communicating with at least one other network sensor of the plurality of network sensors, at least one of the plurality of sensors receiving data from the tracking tag; and a remote server in communication with the mesh network, the remote server processing the signals from the tracking tag communicated over the mesh network, the remote server configured to initiate a new process when a sterilization event is detected, configured to associate the sterilizable object with a mobile object, configured to add data to a database, configured to update a user interface, and configured to change the state of a process;

wherein the sterilization event is one of ultrasonic energy sterilization, steam sterilization, heat sterilization, pressure sterilization, chemical sterilization and hot water sterilization, and wherein an ultrasonic energy sterilization has a sterilization threshold value of a detection of a pre-established amount of ultrasonic energy, a steam sterilization has a sterilization threshold value of a detection of a temperature of at least 100° C., a heat sterilization has a sterilization threshold value of a detection of a temperature of at least 150° C., a pressure sterilization has a sterilization threshold value of a detection of a pressure of at least 1.036 Bar above atmospheric pressure, a chemical sterilization has a sterilization threshold value of a detection of hydrogen peroxide in a concentration amount of at least 6%, and a hot water sterilization has a sterilization threshold value of a detection of a temperature of at least 70° C.

\* \* \* \* \*